US007753926B1

(12) United States Patent
    Pacetti

(10) Patent No.: US 7,753,926 B1
(45) Date of Patent: Jul. 13, 2010

(54) METHOD AND APPARATUS FOR TREATING VULNERABLE PLAQUE

(75) Inventor: Stephen Dirk Pacetti, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1169 days.

(21) Appl. No.: 10/459,171

(22) Filed: Jun. 10, 2003

(51) Int. Cl.
    *A61M 29/00* (2006.01)
    *A61B 17/22* (2006.01)
(52) U.S. Cl. ...................................... 606/159; 606/194
(58) Field of Classification Search ............. 604/101.1, 604/103.08; 606/159, 191, 194, 192, 200
    See application file for complete search history.

(56) References Cited

U.S. PATENT DOCUMENTS

| 4,423,725 A | * | 1/1984 | Baran et al. ............ 128/207.15 |
| 4,983,167 A | * | 1/1991 | Sahota ....................... 606/194 |
| 5,190,540 A | * | 3/1993 | Lee ............................ 606/28 |
| 5,273,536 A |   | 12/1993 | Savas |
| 5,334,146 A |   | 8/1994 | Ozasa |
| 5,338,298 A |   | 8/1994 | McIntyre |
| 5,415,635 A | * | 5/1995 | Bagaoisan et al. ...... 604/101.05 |
| 5,470,313 A |   | 11/1995 | Crocker et al. |
| 5,501,667 A | * | 3/1996 | Verduin, Jr. ............ 604/101.01 |
| 5,525,388 A |   | 6/1996 | Wand et al. |
| 5,549,551 A | * | 8/1996 | Peacock et al. ........ 604/103.05 |
| 5,645,560 A |   | 7/1997 | Crocker et al. |
| 5,797,878 A |   | 8/1998 | Bleam |
| 5,843,116 A |   | 12/1998 | Crocker et al. |
| 6,036,697 A | * | 3/2000 | DiCaprio .................... 606/108 |
| 6,616,682 B2 | * | 9/2003 | Joergensen et al. ......... 606/200 |
| 6,694,181 B2 | * | 2/2004 | Kokate et al. ............... 600/547 |
| 6,905,476 B2 |   | 6/2005 | Ponzi |
| 6,972,024 B1 | * | 12/2005 | Kilpatrick et al. ........... 606/192 |
| 2002/0072707 A1 | * | 6/2002 | Gonzalez et al. ....... 604/103.06 |
| 2003/0171765 A1 | * | 9/2003 | Kokate et al. ............... 606/159 |

OTHER PUBLICATIONS

Mandrusov, Membrane-Based Cell Affinity Chromatography to Retrieve Viable Cells, Biotechnol, Prob. 1995, 11, 208-213, Artificial Organs Research Laboratory, Department of Chemical Engineering, Material Science and Metallurgy, Columbia University, New York, New York 10027, and Lousville, Lousville, Kentucky 40292.

Assmus, Transplantation of Progenitor Cells and Regeneration Enhancement in Acute Myocardial Infarction (TOPCARE-AMI), Clinical Investigation and Reports, Oct. 8, 2002, pp. 3009-3017, Department of Molecular Cardiology and Department of Hematology (H.M., D.H.) University of Frankfurt, Frankfurt, Germany, Circulation available at http://www.circulationha.org. DOI: 10.1161/01. CIR.0000043246.74879CD.

* cited by examiner

*Primary Examiner*—(Jackie) Tan-Uyen T Ho
*Assistant Examiner*—Melissa Ryckman
(74) *Attorney, Agent, or Firm*—Blakely Sokoloff Taylor & Zafman LLP

(57) ABSTRACT

Embodiments include, a medical device having a balloon portion with a first end, a second end, and a variable balloon mass to inflate the balloon portion non-uniformly from the first end to the second end. In one embodiment, the balloon portion inflates in a controlled manner to rupture a vulnerable plaque near the second end.

17 Claims, 20 Drawing Sheets

Trifold

BI FOLD

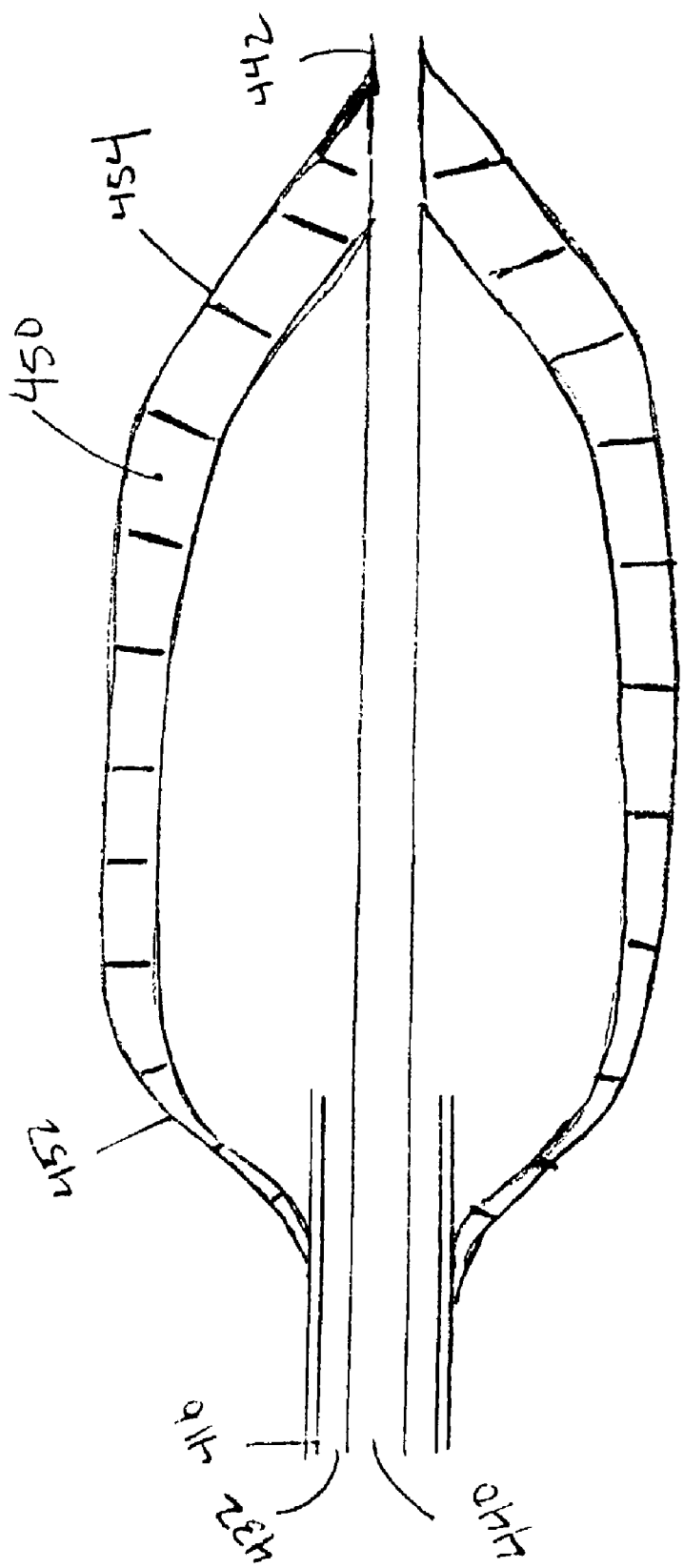

A-A

B-B

C-C

D-D

METHOD AND APPARATUS FOR TREATING VULNERABLE PLAQUE

TECHNICAL FIELD

The invention, in one embodiment, relates generally to the treatment of atherosclerosis such as heart related diseases, and more particularly, in one embodiment, to the treatment of vulnerable plaque.

BACKGROUND

Coronary heart disease is generally thought to be caused by the narrowing of coronary arteries by atherosclerosis, the buildup of fatty deposits in the lining of the arteries. The process that may lead to atherosclerosis begins with the accumulation of excess lipids and cholesterol in the blood. These substances infiltrate the lining of arteries, gradually increasing in size to form deposits commonly referred to as plaque or atherosclerotic occlusions. Plaques narrow the arterial lumen and impede blood flow. Thrombus can accumulate on the lesion, eventually creating a blood clot that may block the artery completely.

The phenomenon of "vulnerable plaque" has created new challenges in recent years for the treatment of heart disease. Unlike occlusive plaques that impede blood flow, vulnerable plaque develops within the arterial walls, but it often does so without the characteristic substantial narrowing of the arterial lumen and resulting symptoms. As such, conventional methods for detecting heart disease, such as an angiogram, may not detect vulnerable plaque growth into the arterial wall. After death, histological examination of the heart can reveal the presence of intact and ruptured vulnerable plaques in the coronary arteries.

The intrinsic histological features that may characterize a vulnerable plaque include increased lipid content, increased macrophage, foam cell and T-lymphocyte content, and reduced collagen and smooth muscle cell ("SMC") content. This fibroatheroma type of vulnerable plaque is often referred to as "soft," having a large lipid pool covered by a fibrous cap. The fibrous cap contains mostly collagen, whose reduced concentration combined with macrophage derived enzyme degradation can cause the fibrous cap of these lesions to rupture under unpredictable circumstances. When ruptured, the lipid core contents, thought to include tissue factor, contact the arterial bloodstream, cause a blood clot to form that can completely block the artery resulting in an acute coronary syndrome ("ACS") event. This type of atherosclerosis is coined "vulnerable" because of the unpredictable tendency of the plaque to rupture. It is thought that hemodynamic and cardiac forces, which yield circumferential stress, shear stress, and flexion stress, may cause disruption of a fibroatheroma type of vulnerable plaque. These forces may rise as the result of simple movements, such as getting out of bed in the morning, or in vivo forces related to blood flow and the beating of the heart. It is thought that plaque vulnerability in fibroatheroma types is determined primarily by factors which include: (1) size and consistency of the lipid core; (2) thickness of the fibrous cap covering the lipid core; and (3) inflammation and repair within the fibrous cap.

FIGS. 1A-1C illustrate the bursting of a vulnerable plaque and the blockage of blood flow by the resulting scar tissue. FIG. 1A illustrates the growth of a vulnerable plaque within the vessel wall. As is typical of vulnerable plaque, it does not extend far out into the vessel lumen to obstruct blood flow (as indicated by the directional arrows). FIG. 1B illustrates the rupturing of the vulnerable plaque, and in this case, in a direction against blood flow. This event alone may cause an occlusive thrombosis. Alternatively, the ruptured contents may be washed downstream by the blood flow (if the ruptured contents are relatively small) without any harmful effects. However, as illustrated by FIG. 1C, the fibrous cap that remains as dissected edges, and torn flaps, can protrude into the blood flow, or even form pockets that further increase the chances of an occlusive clot formation. The interior lining of the fibrous cap, and lipid pool, has no coverage of endothelial cells. In addition to mechanical obstructions, all of these surfaces are highly thrombogenic. As such, the therapeutic rupture of a vulnerable plaque might be a viable treatment method if not for the uncontrolled mechanics of the rupture, exposing thrombogenic surfaces, creating issue flaps and dissection, and even forming occlusive pockets. The prior art does not provide for a device or technique to treat vulnerable plaque by rupturing it in a controlled manner while minimizing harmful side effects.

SUMMARY

Embodiments of a medical device having a balloon portion with a first end, a second end, and a variable balloon mass to inflate the balloon portion non-uniformly from the first end to the second end are described. In one embodiment, the balloon portion inflates in a controlled manner to rupture a vulnerable plaque near the second end. In an alternative embodiment, at least one balloon is disposed near a distal portion of a catheter. The balloon inflates from a proximal end to a distal end to rupture a vulnerable plaque near the distal end and in the direction of blood flow.

Additional embodiments, features, and advantages of the medical device will be apparent from the accompanying drawings, and from the detailed description that follows below.

BRIEF DESCRIPTION OF THE DRAWINGS

The invention may best be understood by referring to the following description and accompanying drawings that are used to illustrate embodiments of the invention. In the drawings:

FIG. 7C illustrates another embodiment of a balloon catheter that may used for the controlled bursting of a vulnerable plaque.

DETAILED DESCRIPTION

In the following description, numerous specific details are set forth such as examples of specific components, processes, etc. in order to provide a thorough understanding of various embodiments of the present invention. It will be apparent, however, to one skilled in the art that these specific details need not be employed to practice various embodiments of the present invention. In other instances, well known components or methods have not been described in detail in order to avoid unnecessarily obscuring various embodiments of the present invention. The term "coupled" as used herein means connected directly to or indirectly connected through one or more intervening components, structures or elements.

Apparatuses and methods for treating vulnerable plaque are described. In one embodiment of the present invention, a vulnerable plaque is ruptured in a controlled manner. Embodiments of the present invention also include a medical device that provides percutaneous treatment for vulnerable plaque. Embodiments of the present invention prevent dissections and torn tissue flaps from blocking blood flow, while minimizing the exposure of thrombogenic surfaces, after the vulnerable plaque has been ruptured. In one embodiment of the present invention, a medical device in the form of a balloon catheter, disposed along a length of a vulnerable plaque, inflates in a controlled manner from a proximal end towards the distal end, and in the same direction of the blood flow. This causes the vulnerable plaque to rupture towards the distal end of the balloon and fibrous cap, and consequently in the same direction as the blood flow. In doing so, the fibrous cap is preferentially ruptured at its distal edge, or side edges. As such, one embodiment of the medical device described herein provides the advantage of controlling the point at which the contents of a vulnerable plaque are squeezed out, or released into the bloodstream. Furthermore, torn tissue flaps, dissections, or vulnerable plaque tissue (e.g., plaque cap) may not form in a manner that will obstruct blood flow at the treatment site. Treatment of a vulnerable plaque with a percutaneous balloon catheter can also cause lipid redistribution external to the blood vessel. In one embodiment of the present invention, the balloon catheter may be advanced percutaneously to the target vulnerable plaque to avoid the need for invasive surgery. In another embodiment, the balloon portion of the catheter is strong and reliable under varying amounts of pressure and is also capable of forming a variety of expandable shapes.

Figure 1A:
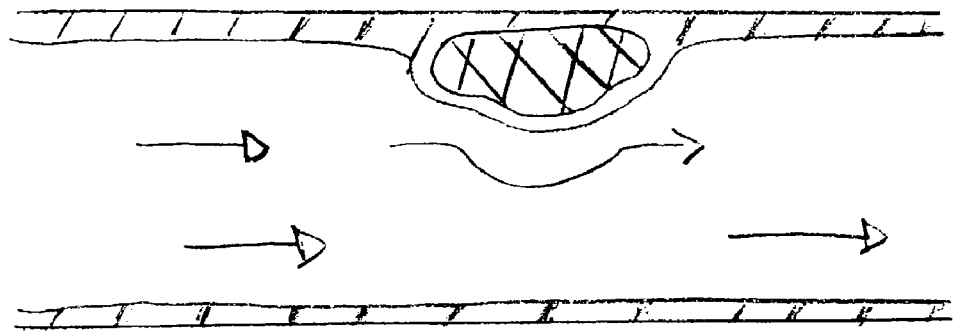
FIGS. 1A-1C illustrate the bursting of a vulnerable plaque and the downstream blockage of blood flow.
Figure 1B:
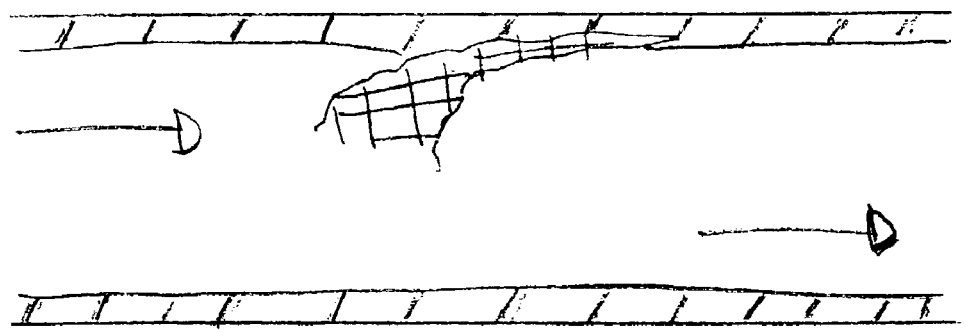
Figure 1C:
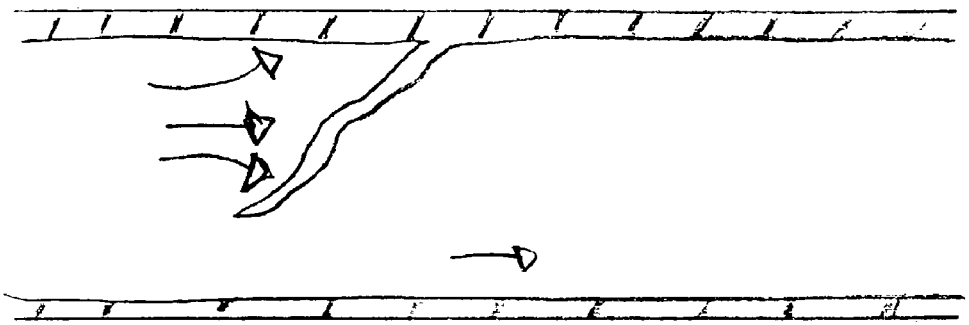
Figure 2A:
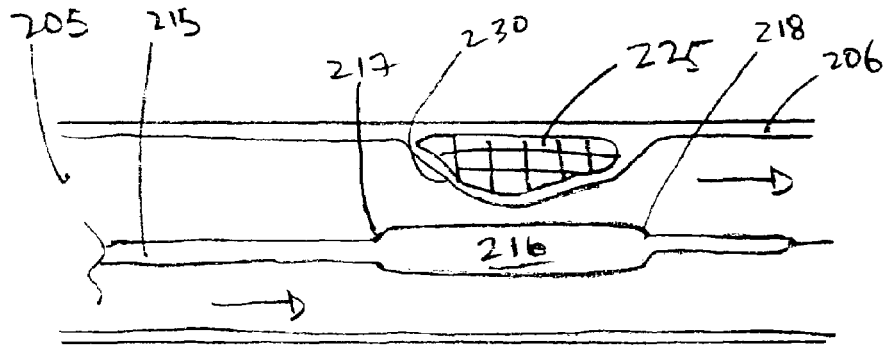
FIG. 2A illustrates one embodiment of a method for the controlled bursting of a vulnerable plaque.
Figure 2B:
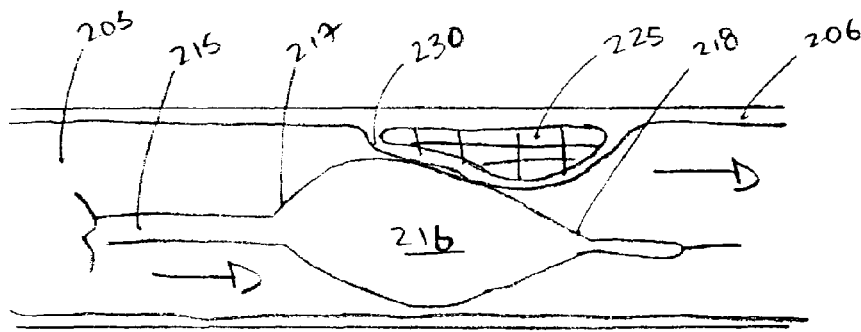
FIG. 2B illustrates one embodiment of a method for the controlled bursting of a vulnerable plaque.
Figure 2C:
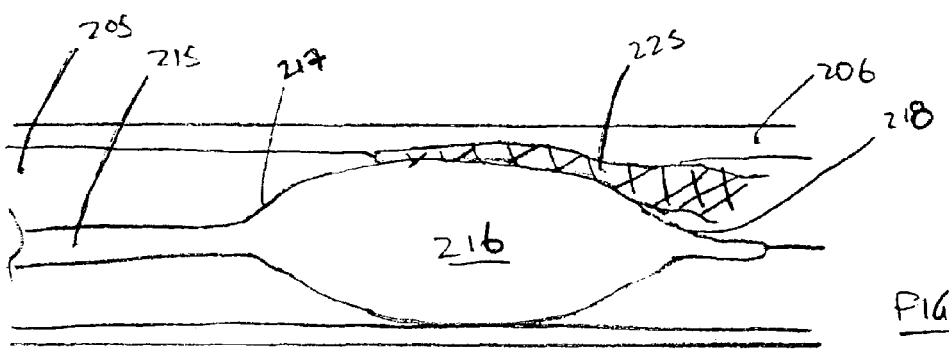
FIG. 2C illustrates one embodiment of a method for the controlled bursting of a vulnerable plaque.

FIGS. 2A-2D illustrate cross-sectional views of one embodiment of a medical device that may control the bursting of a vulnerable plaque into the bloodstream. FIG. 2A illustrates arterial wall 206 that forms a lumen 205 for blood flow in the direction of the arrows indicated. Vulnerable plaque 225 has formed within arterial wall 206 with plaque cap 230 facing arterial lumen 205. In one embodiment, the medical device is a balloon catheter having catheter portion 215 and balloon 216. The balloon 216 has a proximal end 217 and distal end 218. Balloon 216 is positioned along a length of vulnerable plaque 225. Proximal end 217 of balloon 216 is shown slightly inflated to form a tapered shape from proximal end 217 to distal end 218. FIG. 2B illustrates proximal end 217 of balloon 216 substantially inflated that causes vulnerable plaque 225 to be pushed toward distal end 218 of balloon 216. FIG. 2C shows balloon 216 completely inflated from its proximal end 217 to its distal end 218. Vulnerable plaque 225 has now been squeezed toward distal end 218 of balloon 216.

Figure 2D:
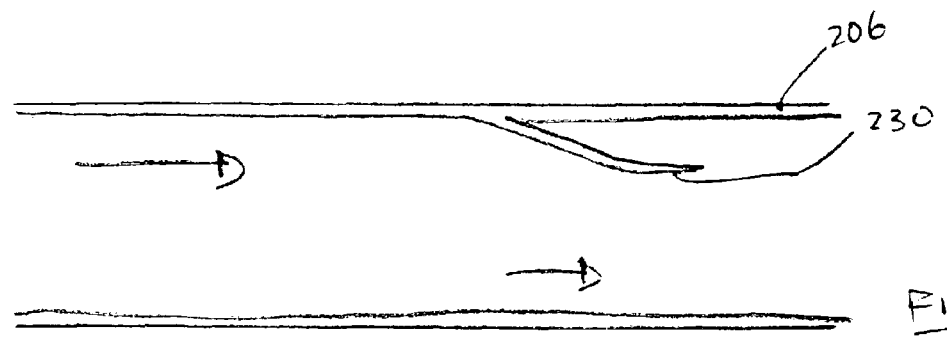
FIG. 2D illustrates one embodiment of a method for the controlled bursting of a vulnerable plaque.

The pressure formed in vulnerable plaque 225 by inflating balloon 216 causes vulnerable plaque 225 to rupture. Particularly, vulnerable plaque 225 has ruptured into arterial lumen 205 near distal end 218 of balloon 216, in a direction with the blood flow. FIG. 2D shows arterial lumen 205 with the balloon catheter removed. What remains of the vulnerable plaque is the remnants of the fibrous cap, here shown in cross section. Because the vulnerable plaque lipid core was squeezed out at primarily the distal edge of the lesion, tissue tears are limited to this area, and the rest of the plaque cap is largely intact. As such, the plaque cap is less likely to obstruct blood flow. If the vulnerable plaque were ruptured in an uncontrolled, random manner, the fibrous cap can be torn into tissue flaps or form a pocket that obstructs blood flow.

Various techniques may be utilized to detect the presence and location of vulnerable plaque. For example, an ultrasound probe ("IVUS") or an optical coherence tomography probe ("OCT") may be guided through the arteries to scan for vulnerable plaque. Alternatively, magnetic resonance imaging ("MRI") devices may be able to detect vulnerable plaque. Near Infrared spectroscopy is another technique for detecting vulnerable plaque. For example, certain wavelengths of light penetrate the arterial wall and produce a specific chemical signature that could correlate to vulnerable plaque composition. Additionally, thermography may also be used to detect vulnerable plaque. Plaques that rupture tend to be inflamed, and data indicates this correlates to a higher temperature compared to non-vulnerable type plaques that do not rupture. As such, a temperature sensitive probe that measures the temperature of arteries could indicate the presence of vulnerable plaque. Alternatively, liquid crystal thermography methods may also be used. For example, a balloon material made of a thermochromic liquid crystal material may be able to optically detect property changes when exposed to increases in temperature. When the balloon contacts a vulnerable plaque, the higher temperature of the vulnerable plaque may be detected by analyzing a beam of light directed towards the suspected vulnerable plaque region and the balloon material in contact therewith. The light may undergo a color change in the balloon material as a result of the higher temperature. Any one of these detectors of vulnerable plaque may be integrated into a catheter such as the device shown in FIGS. 2A-2D or other embodiments described herein.

Figure 3:
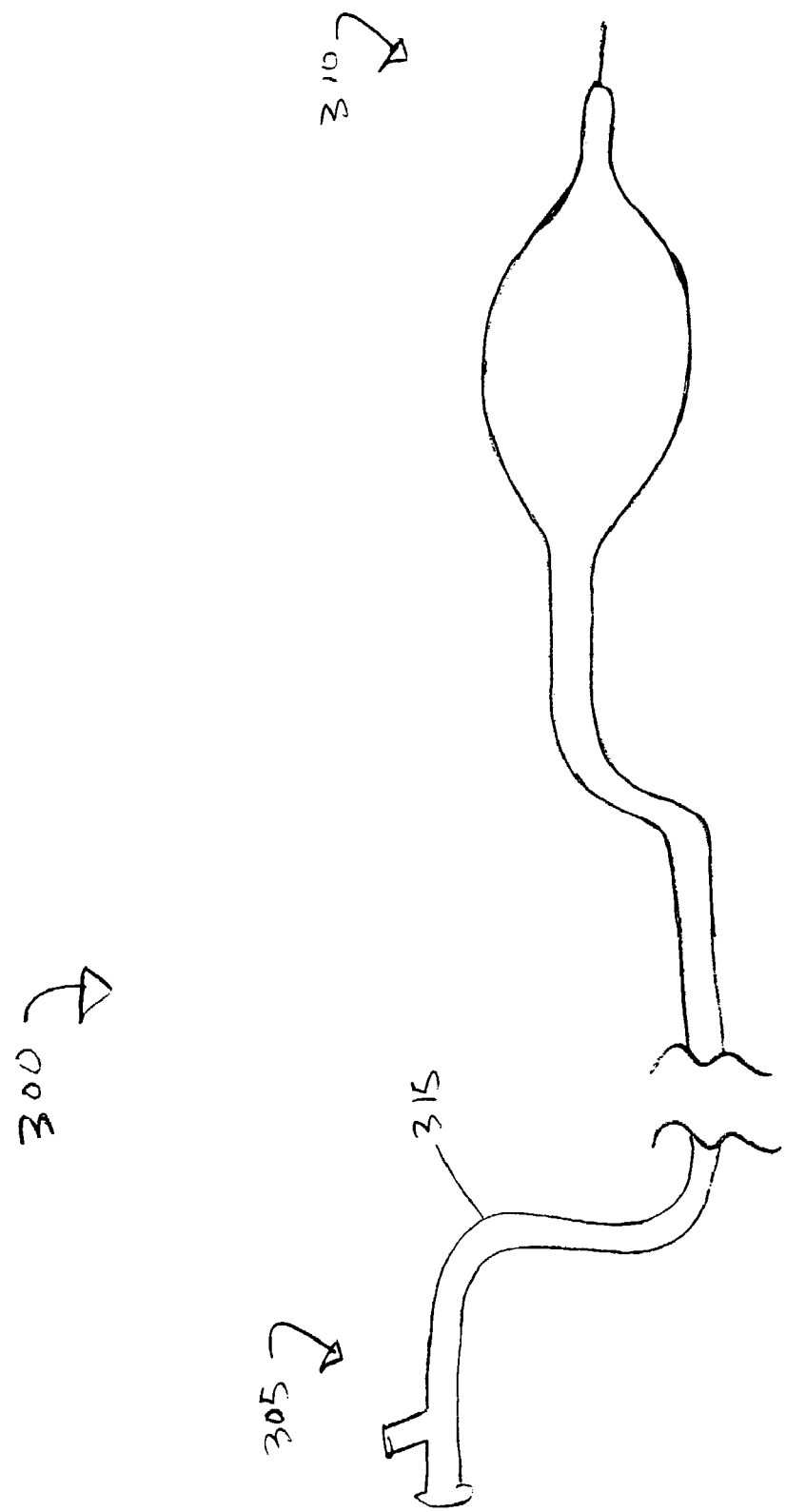
FIG. 3 illustrates one embodiment of a medical device that may be used to control the bursting of a vulnerable plaque.
Figure 3A:
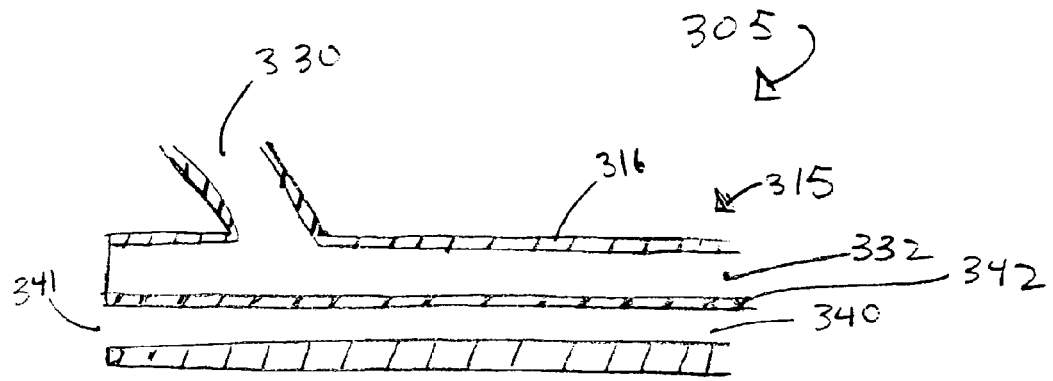
FIG. 3A illustrates a proximal portion of the medical device shown in FIG. 3.
Figure 3B:
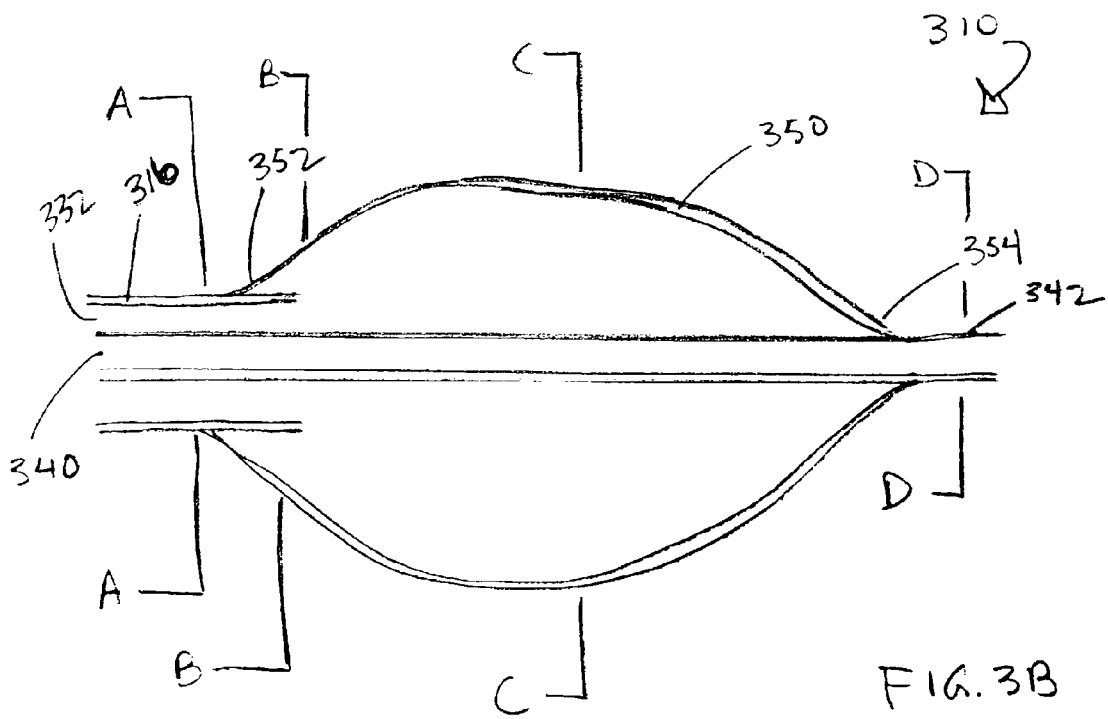
FIG. 3B illustrates a distal portion of the medical device shown in FIG. 3.

FIG. 3 illustrates a perspective view of one embodiment of the present invention that may be used to rupture the vulnerable plaque in a controlled manner. In one embodiment, the present invention is a percutaneous medical device in the form of a balloon catheter 300. Balloon catheter 300 has a proximal portion 305, a distal portion 310, and an elongated catheter portion 315. FIG. 3A shows an enlarged view of proximal portion 305 having a port 330 that leads to an inflation lumen 332. An opening 341 may be formed by an inner wall 342 to form a guidewire lumen 340. A catheter wall 316 may be formed around inflation lumen 332 and guidewire lumen 340. FIG. 3B shows an enlarged view of distal portion 310 having catheter wall 316 that forms inflation lumen 332 with inner wall 342. Inner wall 342 also forms guidewire lumen 340. Inflatable balloon 350 may be disposed near distal portion 310 with a proximal end 352 coupled to catheter wall 316 and distal end 354 coupled to inner wall 342. Inflation lumen 332 is continuous from port 330 near a proximal portion 305 all the way to balloon 350 near distal portion 310. As such, balloon 350 may be inflated by injecting an inflation medium (e.g., a liquid or a gas) into port 330. The inflation medium may be slightly heated relative to normal body temperatures in order to liquefy the lipids in the vulnerable plaque; in one example, the inflation medium may be heated to about 104° F.

Figure 3C:
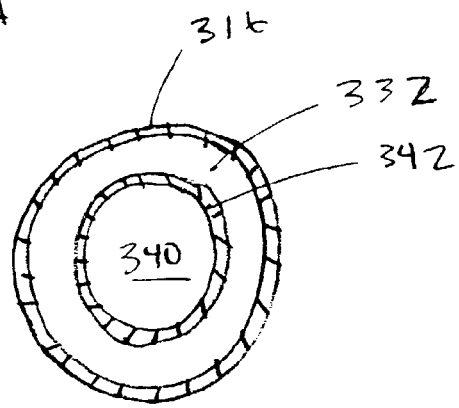
FIG. 3C illustrates a cross-sectional view taken along line A-A of the medical device shown in FIG. 3B.
Figure 3D:
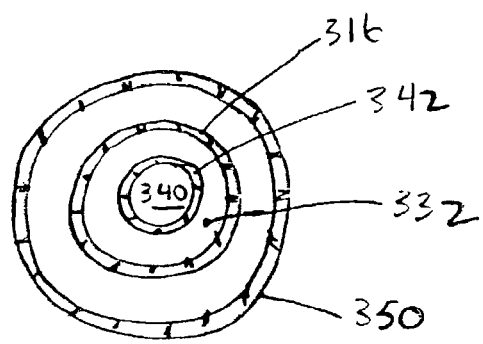
FIG. 3D illustrates a cross-sectional view taken along line B-B of the medical device shown in FIG. 3B.
Figure 3E:
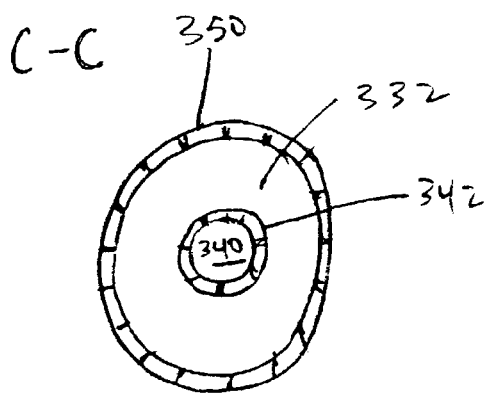
FIG. 3E illustrates a cross-sectional view taken along line C-C of the medical device shown in FIG. 3B.
Figure 3F:
FIG. 3F illustrates a cross-sectional view taken along line D-D of the medical device shown in FIG. 3B.

FIGS. 3C-3F illustrate various cross-sectional views of distal portion 310. FIG. 3C shows a cross-sectional view of distal portion 310 taken along line A-A. This region of balloon catheter 300 has catheter wall 316, inflation lumen 332, inner wall 342, and guidewire lumen 340. FIG. 3D shows a cross-sectional view of balloon catheter 300 taken along line B-B. This region of balloon catheter 300 has balloon 350, inflation lumen 332, catheter wall 316, inner wall 342, and guidewire lumen 340. FIG. 3E shows a cross-sectional view of balloon catheter 300 taking along line C-C. This region of balloon catheter 300 has balloon 350, inflation lumen 332, inner wall 342, and guidewire lumen 340. FIG. 3F shows a cross-sectional view of balloon catheter 300 taking along line D-D. This region of balloon catheter 300 has inner wall 342 and guidewire lumen 340. In one embodiment, inner wall 342 and guidewire lumen 340 extend from a proximal portion 305 to distal portion 310.

In one embodiment of the present invention, balloon catheter 300 may be sized for percutaneous delivery through a blood vessel for advancement to the arterial region (e.g., a coronary artery.) In an alternative embodiment, balloon catheter 300 may be sized for percutaneous delivery to other parts of the human body. In yet another embodiment, a guidewire (not shown) may be initially advanced to the treatment location. Catheter 300 may be loaded and tracked over the guidewire (within guidewire lumen 340) to be positioned near the vulnerable plaque. In other embodiments, catheter 300 may be any of the catheter types used in the art, including but not limited to "rapid exchange" (RX) catheters, "over-the-wire" (OTW) catheters, or a "tip RX" catheters. If a guidewire is utilized, the guidewire may be removed after the distal portion 310 of catheter 300 has reached the target vulnerable plaque. The catheter may, in certain embodiments, include a drug lumen which is continuous from a proximal port to an opening at a distal portion of the catheter. This drug lumen may be used to release heparin or other anticoagulants downstream of the balloon as the balloon is inflated. This will tend to prevent the ruptured contents of the vulnerable plaque from causing a thrombosis. Alternatively, the guidewire lumen may be used as a drug lumen (e.g., after the guidewire is removed from the lumen.) The catheter may also include, in certain embodiments, a perfusion lumen which is coupled to the balloon and which allows blood to flow downstream from the vulnerable plaque while the balloon is inflated.

The catheter assembly can be formed from conventional materials of construction. The material forming the catheter body can be any metal or polymer with ductile properties which would be acceptable for the needs of intravascular devices. Specifically, the material chosen for the catheter body should have sufficient flexibility so it can be easily advanced through tortuous anatomy.

Figure 4A:
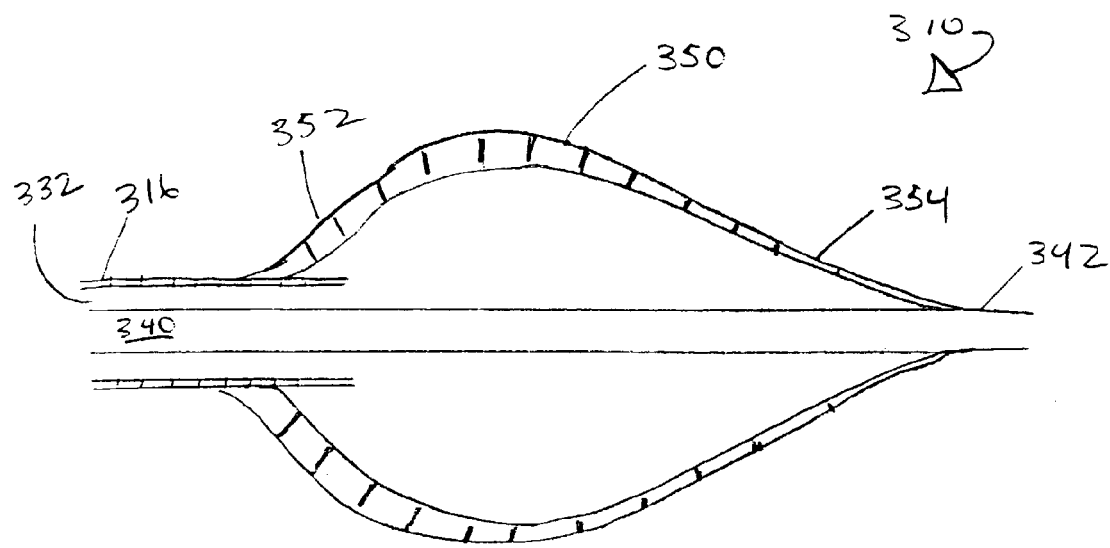
FIG. 4A illustrates one embodiment of a balloon catheter that may used for the controlled bursting of a vulnerable plaque.
Figure 4B:
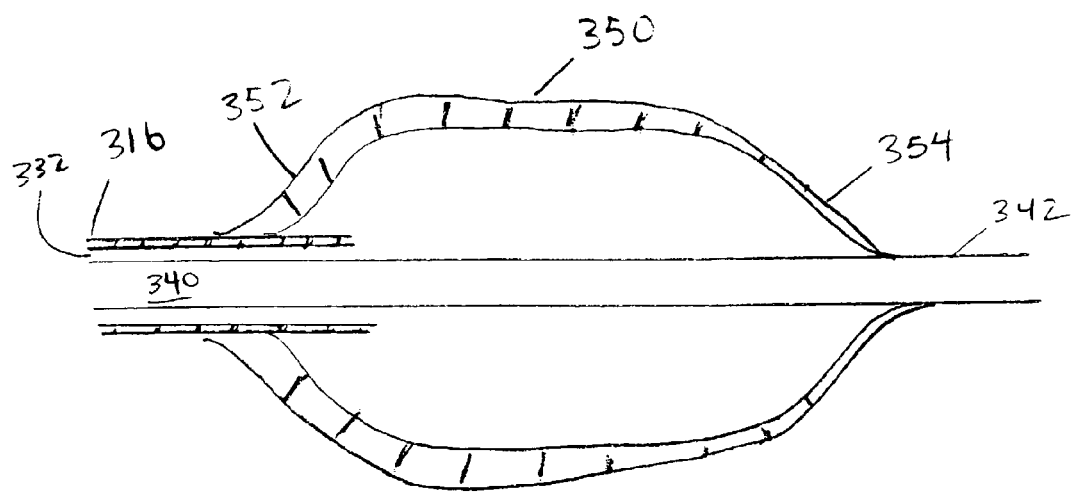
FIG. 4B illustrates one embodiment of a balloon catheter that may used for the controlled bursting of a vulnerable plaque.

FIGS. 4A and 4B illustrate one embodiment of the present invention in which a distal portion 310 of the balloon catheter has a balloon 350 that inflates non-uniformly such that the proximal end 352 inflates first, followed by the distal end 354. In one embodiment, distal portion 310 may be part of balloon catheter 300 described above with respect to FIG. 3. Distal portion 310 has catheter wall 316, inflation lumen 332, inner wall 342, and guidewire lumen 340. Balloon 350 has a proximal end 352 coupled to catheter wall 316 and a distal end 354 coupled to inner wall 342. FIG. 4A shows balloon 350 having a wall thickness that tapers from proximal end 352 towards distal end 354, that is, the thickness of the balloon wall reduces along the balloon length from the proximal end 352 to the distal end 354. Additionally, balloon 350 is molded such that the overall shape of balloon 350 tapers from the proximal end 352 to the distal end 354. As balloon 350 begins to inflate the proximal end 352 inflates first to reach a size as dictated by its material properties. Furthermore, the thickness of balloon 350 near proximal end 352 limits the diameter and size to which it can expand. As the pressure continues to increase with the addition of more and more inflation medium, the distal end 354 of balloon 350 begins to expand to form the fully inflated form of balloon 350 as illustrated in FIG. 4B. This design of a balloon that inflates from proximal to distal requires a balloon with a larger proximal than distal diameter at rest, a thicker balloon wall near proximal end 354, and a balloon material with low to medium compliance.

In one embodiment of the present invention, balloon 350 may be made of elastomeric or compliant material including, but not limited to, nylon 12, nylon 6, nylon 6.6, polyetherblock copolyamide polymers ("Pebax®"), poly(ethylene terephthalate) (Mylar®), polyethylene, polypropylene, polyether urethanes, polycarbonate urethanes, polyester urethanes, silicone urethanes, and polyesters (Hytrel®). In one embodiment, balloon 350 may have a length in the range of 8-30 mm. Varying the distribution of balloon mass from one end to the other may be achieved by a number of methods known in the art. Balloon wall thickness may be made variable (for example, tapered from a proximal end to a distal end) by an extrusion process. Alternatively, a balloon wall thickness may be varied by injection molding. Other methods are known in the art; however, a detailed description is not provided herein.

Figure 5A:
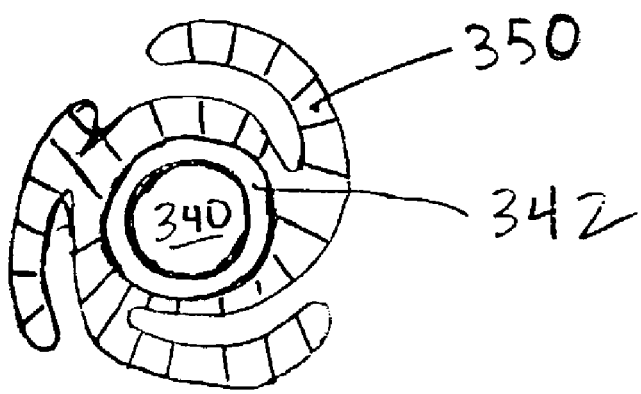
FIG. 5A illustrates a cross-sectional view of the balloon catheter shown in FIGS. 4A-4B.
Figure 5B:
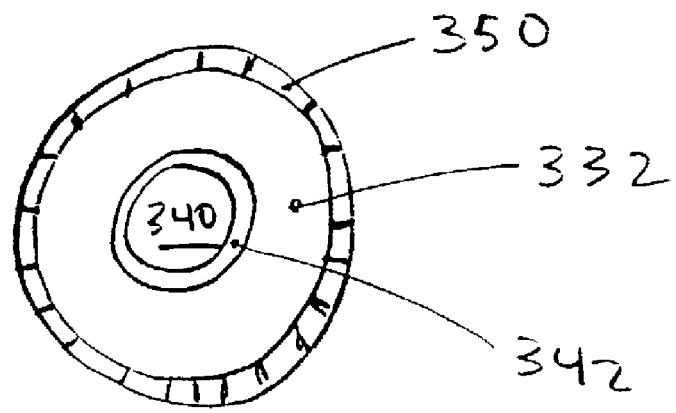
FIG. 5B illustrates a cross-sectional view of the balloon catheter shown in FIGS. 4A-4B.

FIGS. 5A and 5B show cross-sectional views of a balloon in a non-inflated state and a fully inflated state, respectively. To minimize the overall profile of balloon 350 in the non-inflated state, balloon 350 may be folded into a particular pattern. FIG. 5A shows one embodiment of a tri-fold pattern that balloon 350 may have in the non-inflated state. This portion of the balloon has balloon 350, inner wall 342, and guidewire lumen 340. When the fully inflated, as shown in FIG. 5B, the folded balloon portions expand into a substantially circular shape with balloon 350, inflation lumen 332, inner wall 342, and guidewire lumen 340. Although present, inflation lumen 332 is not shown in the non-inflated state of FIG. 5A.

Figure 6A:
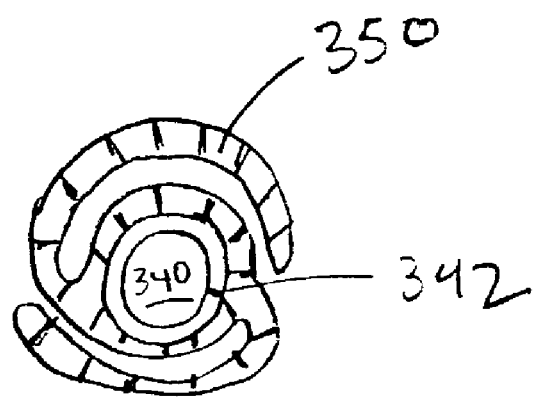
FIG. 6A illustrates an alternative cross-sectional view of the balloon catheter shown in FIGS. 4A-4B.
Figure 6B:
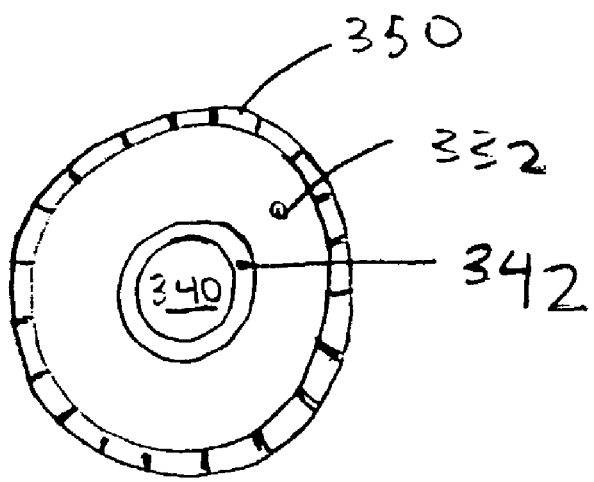
FIG. 6B illustrates an alternative cross-sectional view of the balloon catheter shown in FIGS. 4A-4B.

FIGS. 6A and 6B show cross-sectional views of an alternative embodiment of a folded pattern for a balloon in a non inflated state. In this embodiment balloon 350 forms a bi-fold (twofold instead of three as shown with respect to FIG. 5A). As shown in FIG. 6A the folded configuration has balloon 350 inner wall 342, and guidewire lumen 340. In the fully inflated state as illustrated in FIG. 6B, the balloon portion expands to form the same substantially circular shape as illustrated in FIG. 5B. In the inflated state, balloon portion has balloon 350, inflation lumen 332, inner wall 342, and guidewire lumen 340.

Figure 7A:
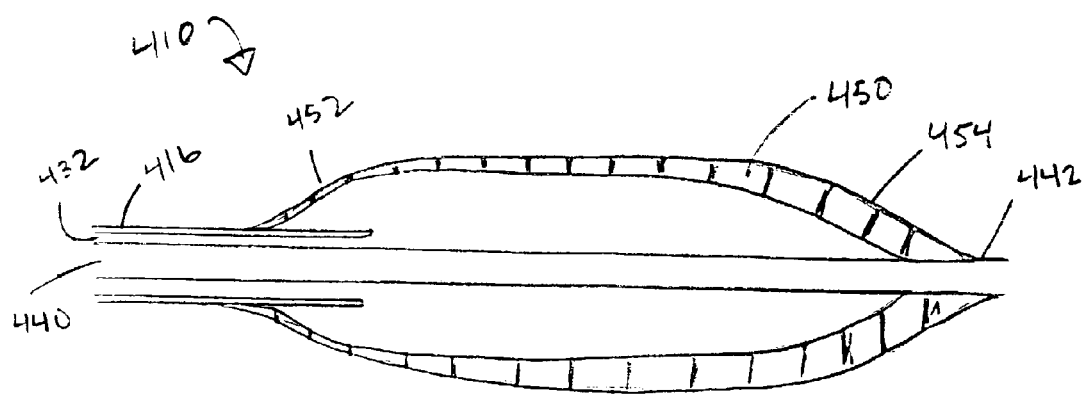
FIG. 7A illustrates another embodiment of a balloon catheter that may used for the controlled bursting of a vulnerable plaque.
Figure 7B:
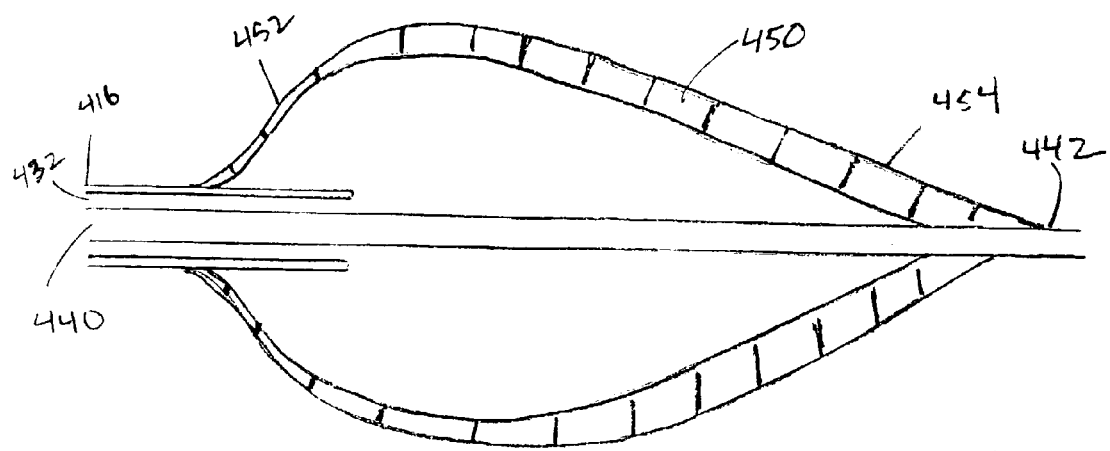
FIG. 7B illustrates another embodiment of a balloon catheter that may used for the controlled bursting of a vulnerable plaque.

FIGS. 7A-7C illustrate cross-sectional views of another embodiment of a medical device that may be used to rupture in a controlled manner. FIG. 7A illustrates a balloon catheter portion 410 in a non-inflated state in which proximal end 452 may have substantially uniform diameter as distal end 454. In the non-inflated state, balloon catheter portion 410 maintains a low profile for advancement through a tortuous anatomy. Balloon catheter 410 includes catheter portion 416 that is coupled to the proximal end 452 of balloon 450. An inner wall 442 may form a guidewire lumen 440 within catheter 416. An inflation lumen 432 may also be formed between catheter 416 and inner wall 442. In this embodiment, the thickness of balloon 450 tapers from the distal end 454 to the proximal end 452. In one embodiment, balloon 450 may be made of a highly elastomeric or high compliant material. Alternatively, proximal end 452 may be composed of high durometer polyurethane or another suitable thermoplastic elastomer such as Pebax®, Hytrel®, and Kraton®. The stress-strain behavior of an elastomer includes an ultimate strain where further elongation stops. This physical property of balloon 450, coupled with the greater distal wall thickness than the proximal wall thickness, results in a balloon 450 which inflates from the proximal end 452 to the distal end 454. In one embodiment, balloon catheter 410, as illustrated, may be part of a medical device in which the balloon catheter portion 410 is the distal portion of an elongated catheter with a proximal portion having input ports, for example, as illustrated in FIG. 3.

FIG. 7B illustrates balloon catheter 410 in a partially inflated state. As an inflation medium is delivered through inflation lumen 432, the proximal end 452 of balloon 450 inflates first. Proximal end 452 of balloon 450 inflates to a predetermined size or diameter based on the material, and the lesser wall thickness of balloon 450 near proximal end 452. FIG. 7C illustrates both proximal end 452 and distal end 454 of balloon 450 fully inflated to a substantially uniform size or diameter. As discussed above, because a thickness of balloon 450 near distal end 454 is greater than proximal end 452, distal end 454 will inflate last. This produces the effect as described with FIGS. 2A-2D (with the vulnerable plaque undergoing rupture near distal end 454).

Figure 8A:
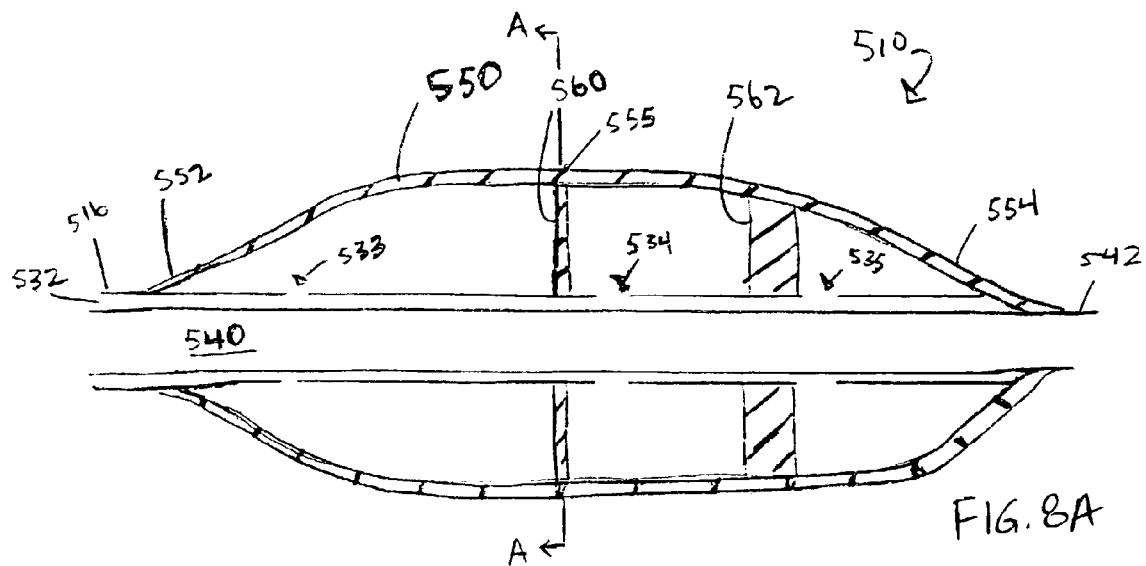
FIG. 8A illustrates another embodiment of a balloon catheter that may used for the controlled bursting of a vulnerable plaque.
Figure 8B:
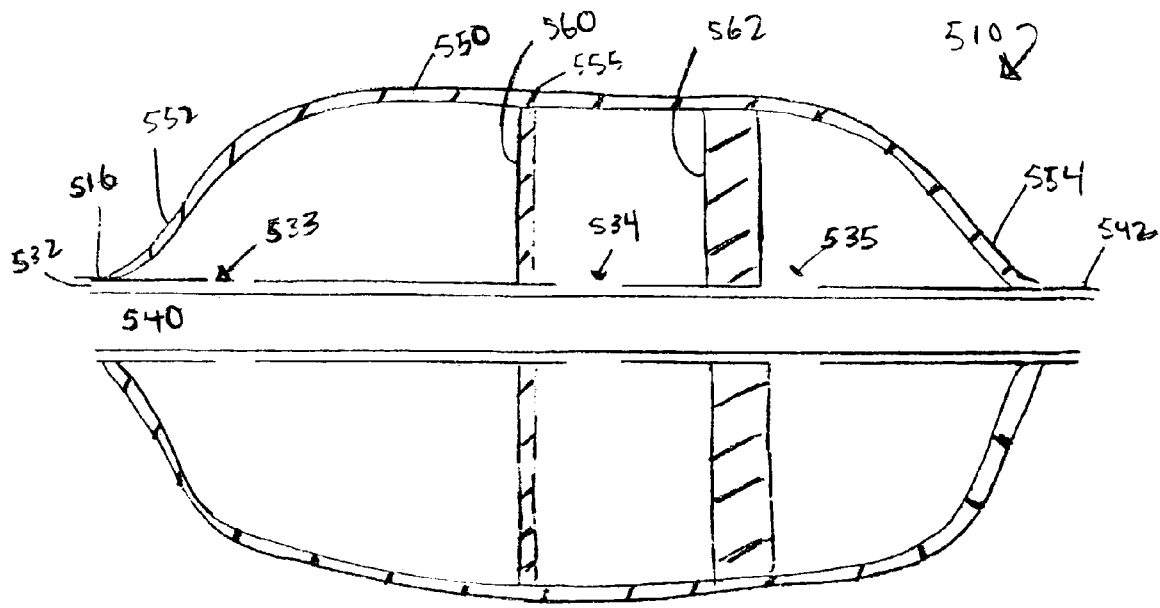
FIG. 8B illustrates another embodiment of a balloon catheter that may used for the controlled bursting of a vulnerable plaque.

FIGS. 8A and 8B illustrate another embodiment of a medical device for rupturing the vulnerable plaque in a controlled manner with an inflatable balloon. FIG. 8A shows a distal portion of a balloon catheter 510 with inflatable balloon 550 disposed on catheter 516. Catheter 516 includes a guidewire lumen 540 formed by an inner catheter wall or tube 542. An inflation lumen 532 may be formed between catheter 516 and inner catheter portion 542. Balloon 550 may have one or more internal members (e.g., 560, 562) to control the elastic resistance of balloon 550. In one embodiment, the elastic members may be elastomeric disk shaped members that extend from a surface of catheter 516 to an inner surface of balloon 550. For example, a first member 560 may be disposed near a central portion 555 of balloon 550, and a second member 562 may be disposed near a distal portion 554 of balloon 550. The internal members form inflation chambers 533, 534, and 535 within balloon 550. First member 560 may have a thickness that is less than the second member 562. Because of the difference in thickness between members 560 and 562, each member may exhibit varying compliance properties. In other words, first member 560 may expand with less pressure applied as compared to second member 562. As such, when an inflation medium is delivered to balloon 550, proximal portion 552 will expand first followed by a central portion 555, and distal portion 554 expanding last. The material properties and thickness of balloon 550 may determine the size and diameter to which balloon 550 fully expands.

FIG. 8B illustrates balloon 550 in a fully inflated state. As discussed above, the varying thickness of internal members 560 and 562 disposed within balloon 550 determines the inflation behavior from proximal portion 552 to distal portion 554. This produces the effect discussed above with respect to FIGS. 2A-2D to rupture the vulnerable plaque in a controlled manner. In one embodiment, inflated balloon 550 may have a substantially cylindrical shape. In an alternative embodiment, balloon 550 may have other shapes.

Figure 9:
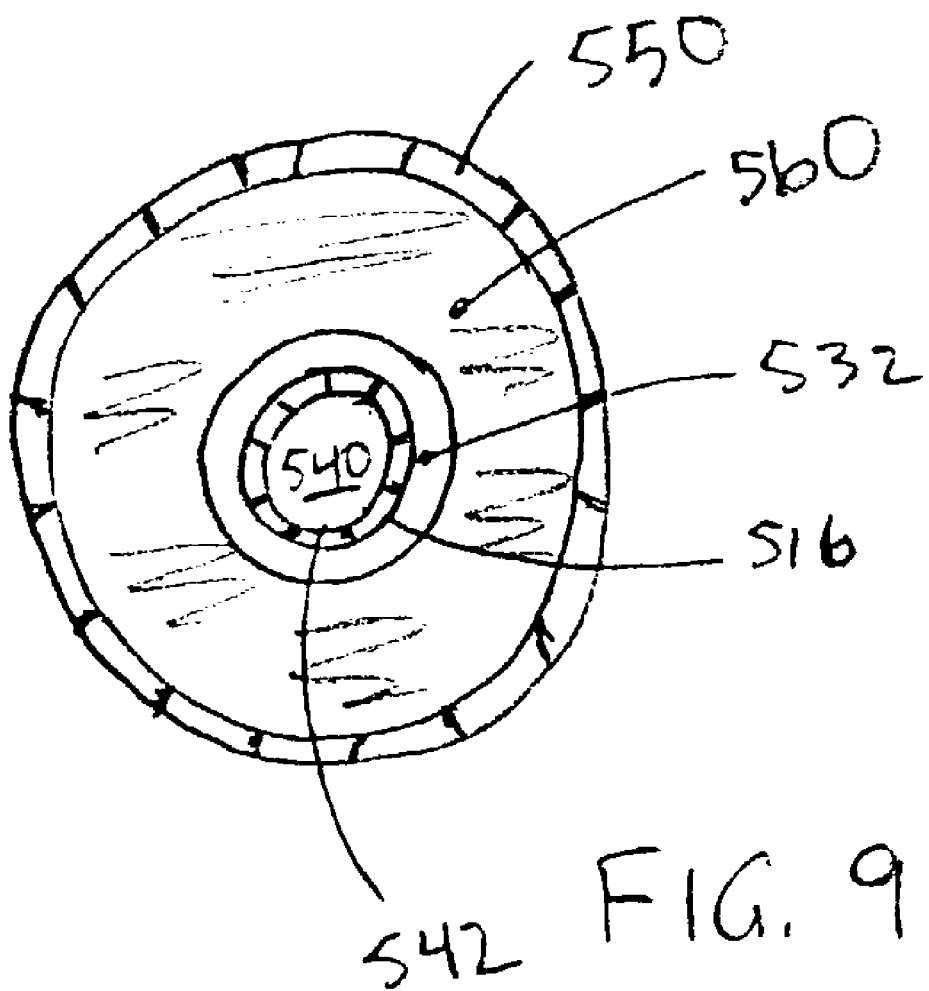
FIG. 9 illustrates a cross-sectional view of the balloon catheter shown in FIGS. 8A-8B.

FIG. 9 illustrates a cross-sectional view of balloon 550 taken along line A-A through first internal member 560. In one embodiment, internal member 560 may be disk-shaped such that internal member 560 makes continuous contact with an inner surface of balloon 550. If the internal members are not solid discs, then chambers 533, 534, and 535 would be in communication with each other and inner tubular member 516 need only extend past the proximal attachment of the balloon. An inflation lumen is formed between catheter 516 and inner wall 542. A guidewire lumen 540 may also be formed by inner catheter 542. The internal members are not limited or restricted to disk shaped structures. It may be appreciated by one of skill in the art that other structural shapes may be used for the internal members. For example, the internal members may be a series of spokes (not shown) disposed around catheter 516 within balloon 550. In another embodiment, alternative structures may be used.

Figure 10A:
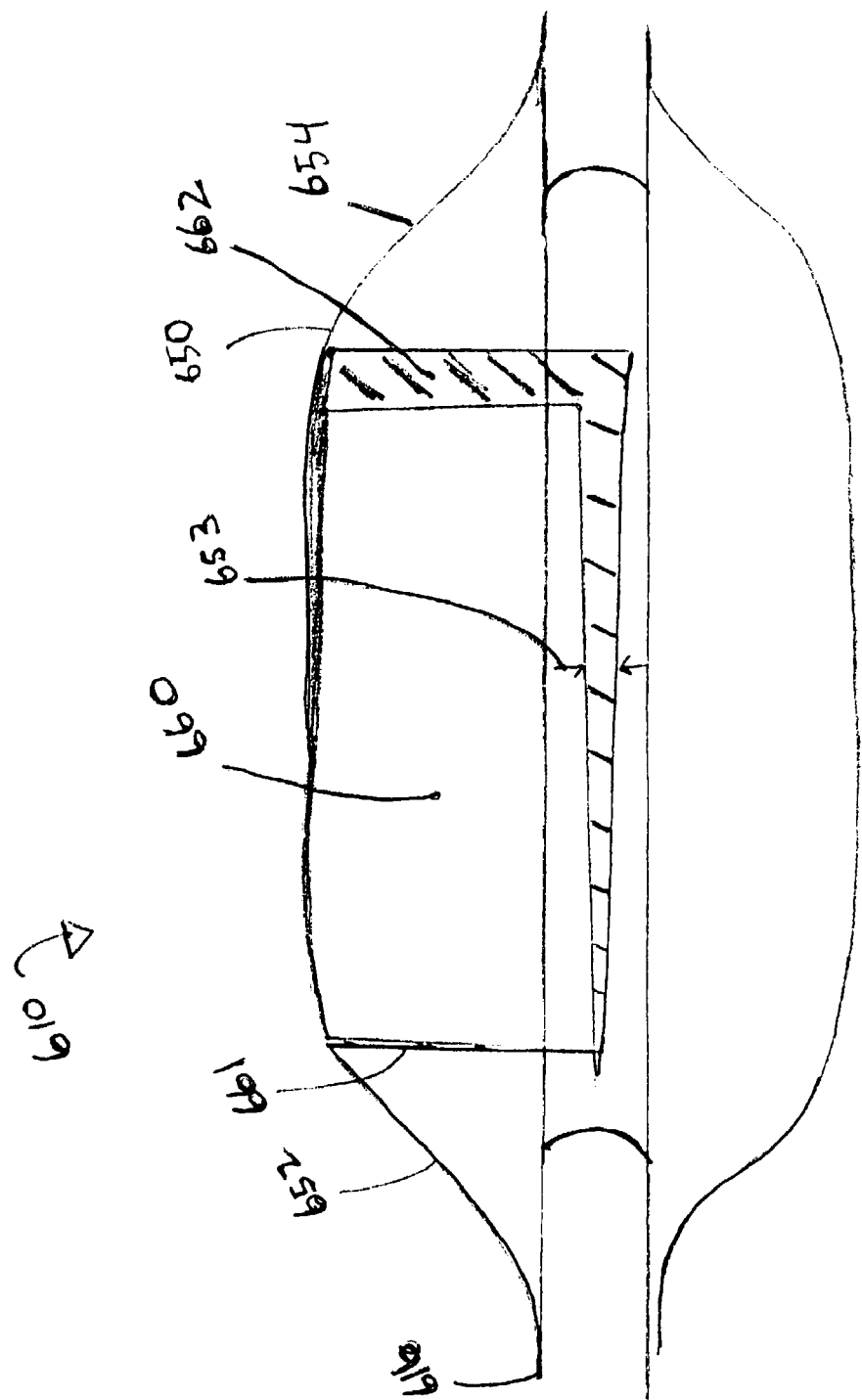
FIG. 10A illustrates another embodiment of a balloon catheter that may be used for the controlled bursting of a vulnerable plaque.

FIG. 10A illustrates an alternative embodiment of a balloon catheter that inflates from a proximal portion towards the distal portion for controlling the bursting of a vulnerable plaque. FIG. 10A illustrates a partial see-through view of balloon catheter portion 610. An inflatable balloon 650 is disposed over catheter 616 with proximal portion 652 and distal portion 654 of balloon 650 coupled to catheter 616. An internal member 660 extends from proximal portion 652 to distal portion 654 of balloon 650. In one embodiment of the present invention, internal member 616 does not extend into the shoulder regions of balloon 650. A thickness 653 of internal member 660 increases from a proximal end 661 towards distal end 662. Internal member 660 also extends from a surface of catheter 616 towards an inner surface of balloon 650. In one embodiment, internal member 660 may be made of an elastomeric material. As such, because proximal end 661 is thinner than distal end 662, balloon 650 inflates first near proximal portion 652 when an inflation medium is injected through an inflation lumen (not shown) to inflate balloon 650. It should be noted that for clarity of description only one internal member is illustrated. However, in alternative embodiments, multiple internal members may be disposed within balloon 650. In one alternative embodiment, 3 internal members may be disposed within balloon 650, spaced approximately 120 degrees around catheter 616.

Figure 10B:
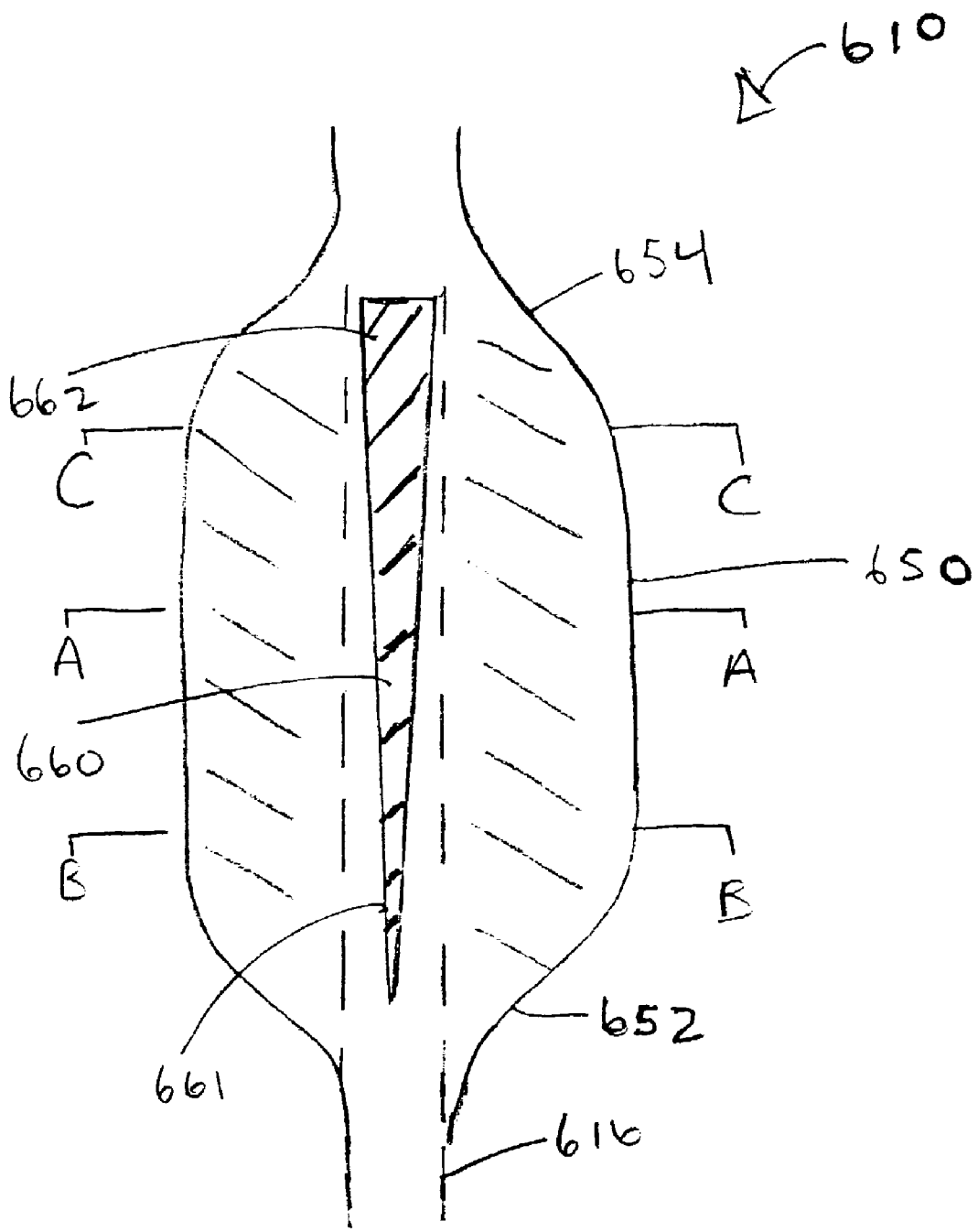
FIG. 10B illustrates another embodiment of a balloon catheter that may be used for the controlled bursting of a vulnerable plaque.

FIG. 10B illustrates a top view of balloon catheter portion 610 described above with respect to FIG. 10A. As illustrated in this partial see-through view, internal member 660 extends along a length of balloon 650 from the proximal portion 652 towards the distal portion 654. A thickness of internal member 660 increases from the proximal end 661 towards the distal end 662. A topside or surface of internal member 660 is coupled to an inner surface of balloon 650 and a bottom surface of internal member 660 is coupled to a surface of catheter 616.

Figure 11A:
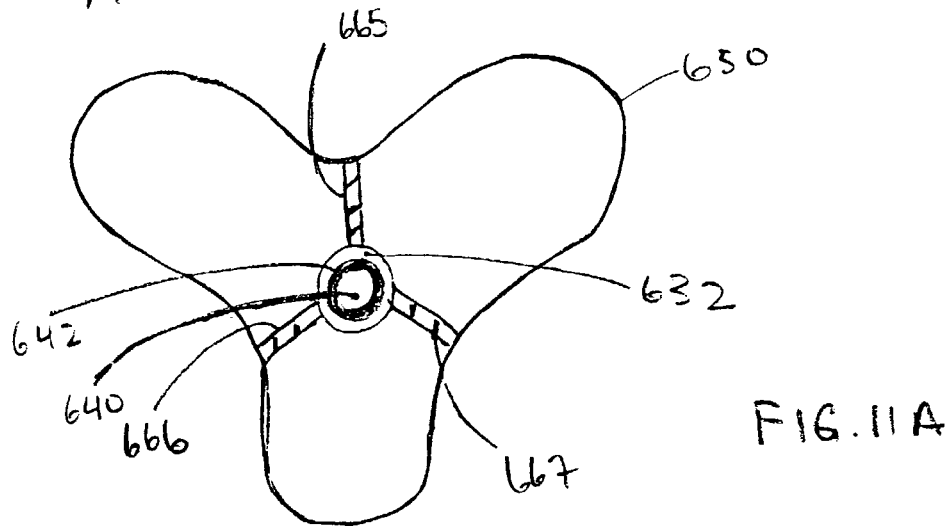
FIG. 11A illustrates a cross-sectional view taken along line A-A of the balloon catheter shown in FIGS. 10A-10B.
Figure 11B:
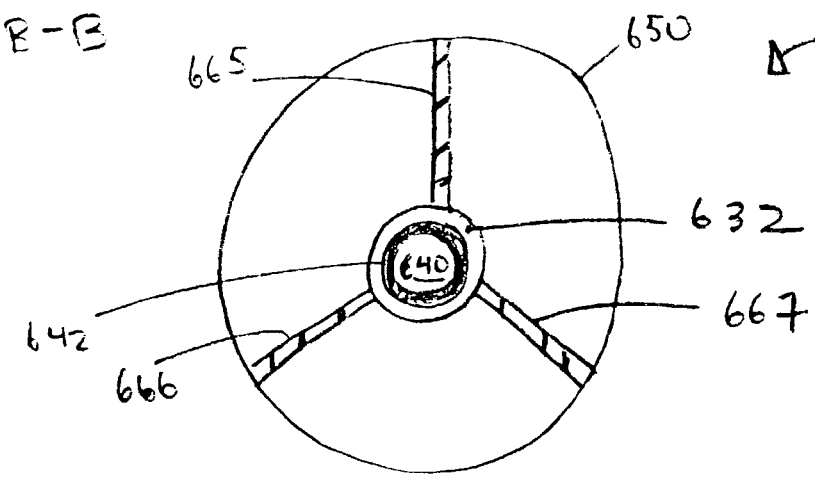
FIG. 11B illustrates a cross-sectional view taken along line B-B of the balloon catheter shown in FIGS. 10A-10B.
Figure 11C:
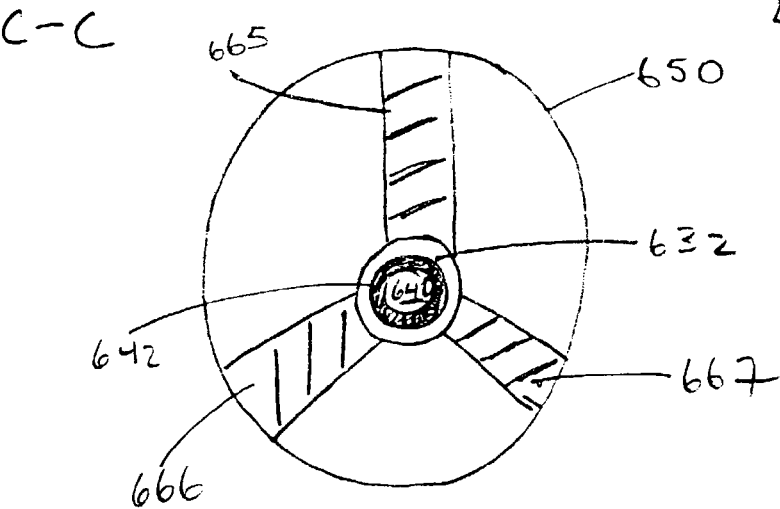
FIG. 11C illustrates a cross-sectional view taken along line C-C of the balloon catheter shown in FIGS. 10A-10B.

FIGS. 11A-11C illustrated cross-sectional views of balloon catheter 610 described above with respect to FIGS. 10A and 10B. FIG. 11A shows a cross-sectional view taken along line A-A of balloon 650 in an un-inflated state. Balloon 650 includes 3 internal members 665, 666, and 667 disposed approximately 120 degrees apart from each other around catheter 616 disposed within balloon 650. A bottom surface of each internal member is coupled to catheter 616, and a top surface is coupled to an inner surface of balloon 650. An inflation lumen 632 is formed between catheter 616 and inner catheter 642 for passing an inflation medium (e.g., a gas or a liquid) into balloon 650. A guidewire lumen 640 may be formed by inner catheter 642 for passing a guidewire therein.

FIGS. 11B and 11C illustrate cross-sectional views of inflated balloon 650 near proximal portion 652 and distal portion 654, respectively. FIG. 11B shows a cross-sectional view of balloon 650 taken along line B-B. Balloon 650 has inflated to a substantially round shape with internal members 665, 666, and 667 expanded radially from catheter 616. A thickness of each internal member is thin compared to the thickness near distal portion 654 as illustrated by FIG. 11C, which shows a cross-sectional view taken along line C-C. In one embodiment, the thickness of the internal members gradually increases from the proximal end 661 to the distal end 662. This variable thickness causes the proximal portion 652 of balloon 650 to inflate first followed by the distal portion 654. When disposed near a targeted vulnerable plaque, balloon 650 inflates to force the vulnerable plaque to burst near the distal portion 654 and in a direction downstream with the blood flow. As discussed above, this controlled rupture minimizes the formation of residual tissue flaps or pockets that may obstruct blood flow after the vulnerable plaque has been drained.

Figure 12A:
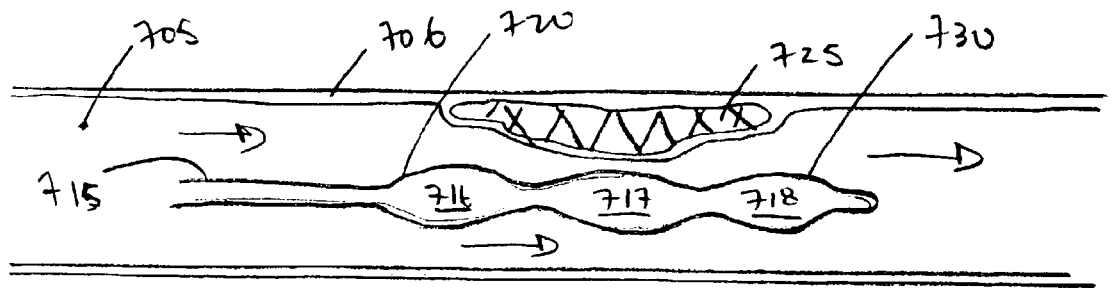
FIG. 12A illustrates another embodiment of a method for the controlled bursting of a vulnerable plaque.
Figure 12B:
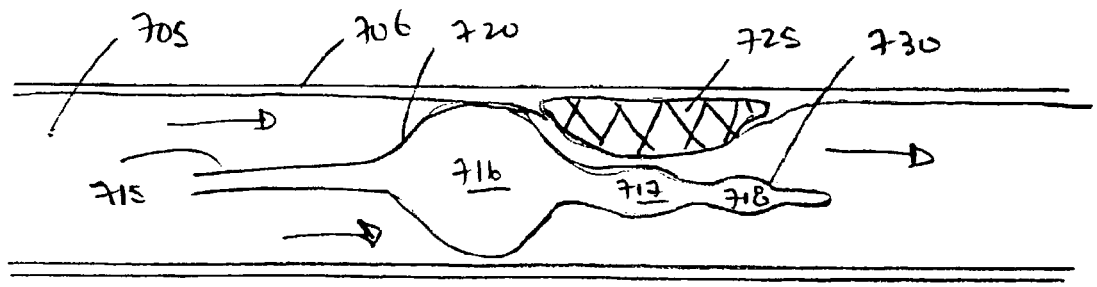
FIG. 12B illustrates another embodiment of a method for the controlled bursting of a vulnerable plaque.
Figure 12C:
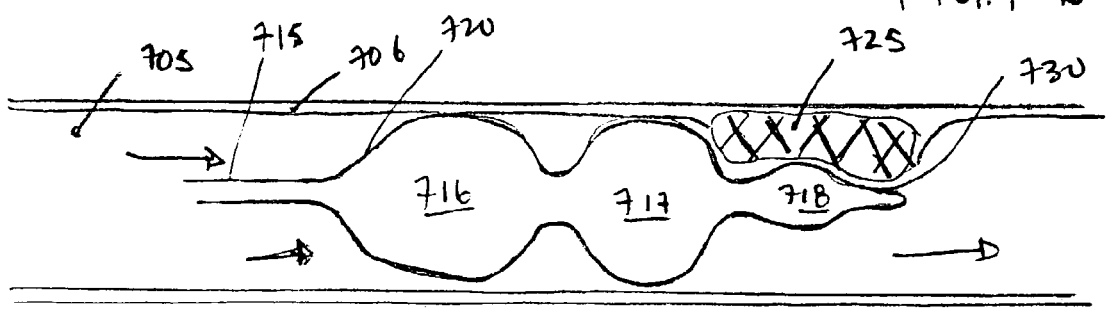
FIG. 12C illustrates another embodiment of a method for the controlled bursting of a vulnerable plaque.
Figure 12D:
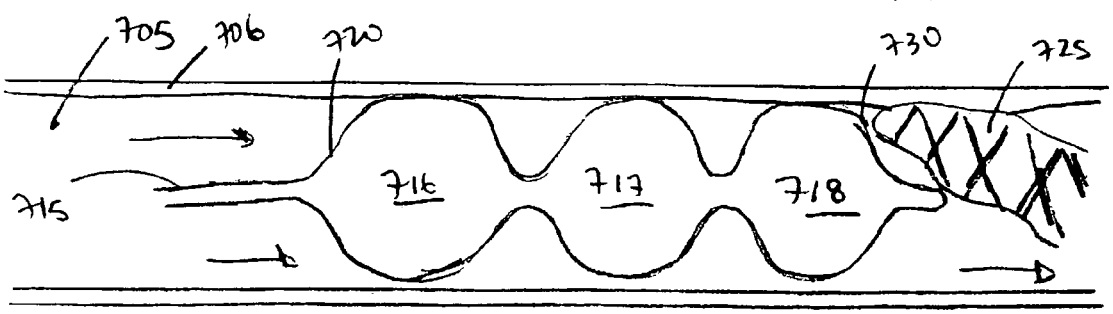
FIG. 12D illustrates another embodiment of a method for the controlled bursting of a vulnerable plaque.

FIGS. 12A-12D illustrate an alternative embodiment of a medical device that ruptures a vulnerable plaque along its distal margin and in a direction of blood flow. A percutaneous medical device in the form of a catheter includes multiple balloons disposed near a distal end. The balloons may be disposed in a linear fashion and allowed to inflate in a particular order. For example, a catheter 715 may have three balloons 716, 717, and 718 disposed linearly along the catheter shaft. To treat a vulnerable plaque 725 that has developed within a blood vessel wall 706, catheter 715 is advanced within the blood lumen 705 such that a proximal portion 720 and prevents the vulnerable plaque 725, from forming tissue flaps, tears, and pockets that obstruct blood flow. Next, as illustrated in FIG. 12B, balloon 716 disposed near proximal portion 720 is inflated first. The inflation of balloon 716 pushes or squeezes vulnerable plaque 725 towards distal portion 730. Next, as illustrated in FIG. 12C, the inflation of balloon 717 continues to push vulnerable plaque 725 towards distal portion 730. FIG. 12D illustrates the inflation of balloon 718 that causes the buildup of enough pressure within vulnerable plaque 725 to cause its rupture. The sequential inflation from balloons 716 to 718 results in vulnerable plaque 725 rupturing in a direction consistent with the blood flow (as indicated by the arrows), and prevents the vulnerable plaque 725 from forming scar tissue that obstructs blood flow.

Figure 13:
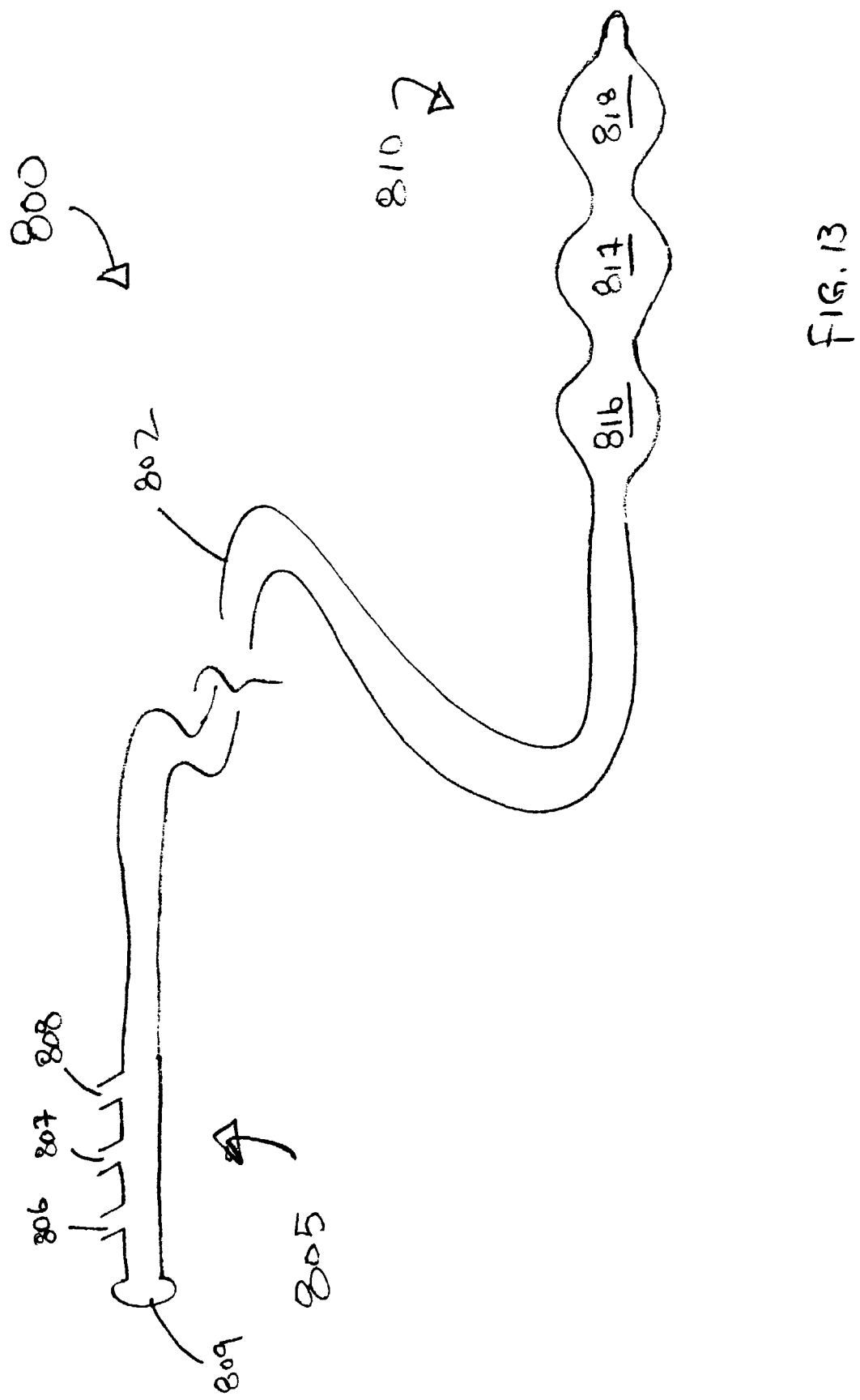
FIG. 13 illustrates another embodiment of a medical device that may be used to control the bursting of a vulnerable plaque.
Figure 13A:
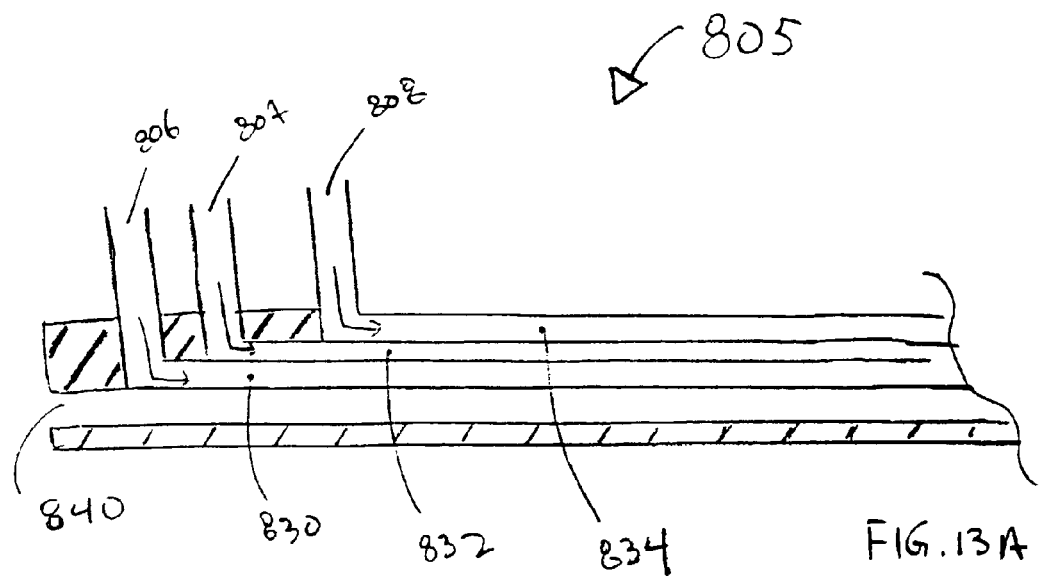
FIG. 13A illustrates a proximal portion of the medical device shown in FIG. 13.

FIG. 13A illustrates a perspective view of a balloon catheter for controlling the rupturing of the vulnerable plaque as described above with respect to FIGS. 12A-12D. Catheter 800 includes a proximal portion 805, an elongated shaft portion 802, and a distal portion 810. Proximal portion 805 has one or more inflation ports for independently inflating balloons disposed near proximal portion 810. For example, catheter 800 may have three inflation ports 806, 807, and 808 for inflating balloons 816, 817, and 818. A guidewire port 809 may also be disposed near proximal portion 805 for inserting a guidewire within shaft portion 802 into the balloons disposed near distal portion 810. In one embodiment, catheter 800 may be sized for percutaneous delivery through a blood vessel for advancement to the arterial region. In an alternative embodiment, catheter 800 may be sized for percutaneous delivery to other parts of the human body. Although catheter 800 illustrates three inflation ports corresponding to three balloons, it may be appreciated that any number of balloons may be disposed near distal portion 810, each having a corresponding inflation port. Alternatively, more than one balloon may be inflated by a single inflation port.

Figure 13B:
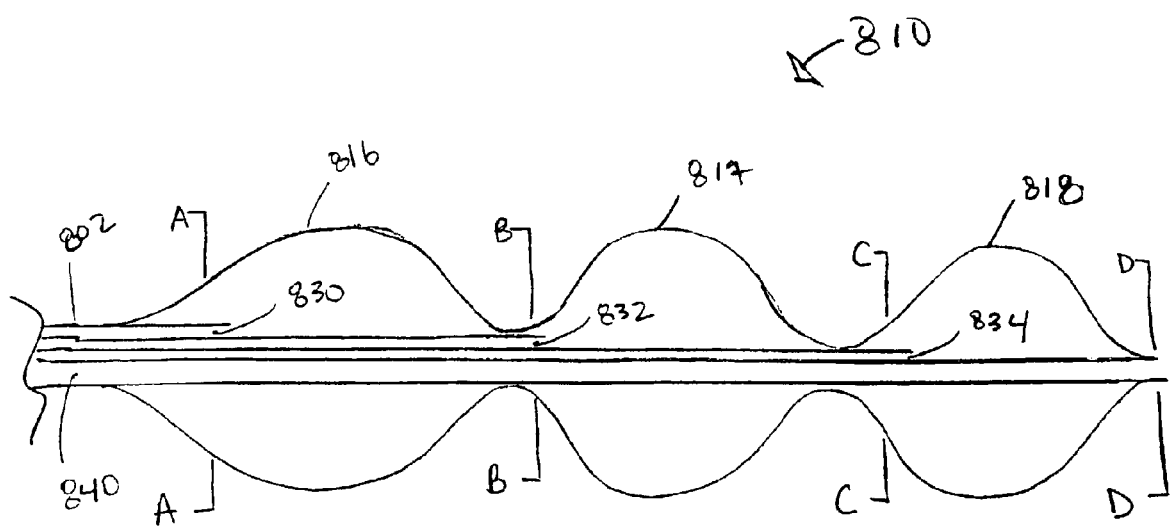
FIG. 13B illustrates a distal portion of the medical device shown in FIG. 13.

FIG. 13A illustrates an enlarged view of proximal portion 805 of catheter 800 shown in FIG. 13. An inflation port 806 leads to inflation lumen 830, port 807 leads to inflation lumen 832, and inflation port 808 leads to inflation lumen 834. A guidewire lumen 840 may also be formed within a center of proximal portion 805. FIG. 13B illustrates an enlarged view of a distal portion 810 of catheter 800 shown in FIG. 13.

Balloons 816, 817, and 818 extend from catheter shaft portion 802. Each balloon and has its own inflation lumen with inflation lumen 830 extending into balloon 816, inflation lumen 832 extending into balloon 817, and inflation lumen 834 extending into balloon 818. Also, guidewire lumen 840 extends within all three balloons and past distal balloon 818. As such, to rupture a vulnerable plaque as illustrated in FIGS. 12A-12D, an inflation medium is inserted first through port 806 and through lumen 830 to inflate balloon 816. Next, inflation medium is inserted into port 807 through lumen 832 to inflate balloon 817. Lastly, inflation medium is inserted through port 808 and through lumen 834 to inflate balloon 818.

Figure 14A:
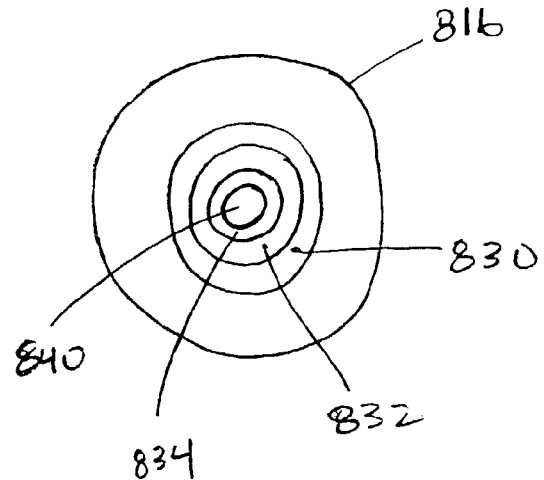
FIG. 14A illustrates a cross-sectional view taken along line A-A of the balloon catheter shown in FIG. 13B.
Figure 14B:
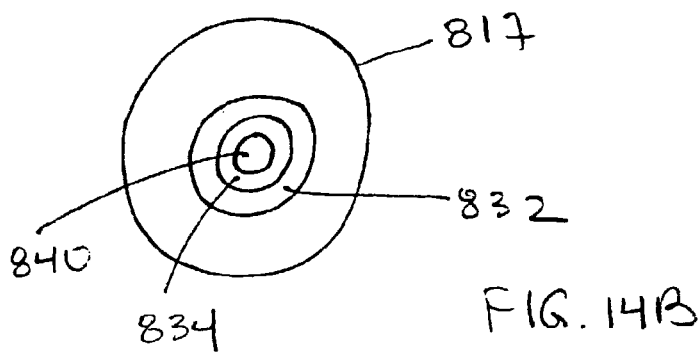
FIG. 14B illustrates a cross-sectional view taken along line B-B of the balloon catheter shown in FIG. 13B.
Figure 14C:
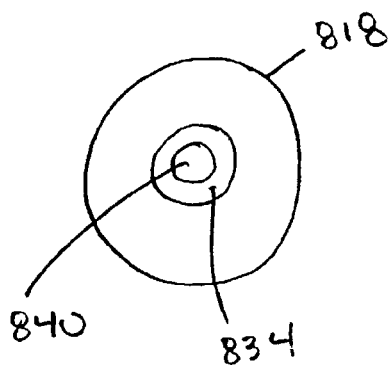
FIG. 14C illustrates a cross-sectional view taken along line C-C of the balloon catheter shown in FIG. 13B.
Figure 14D:
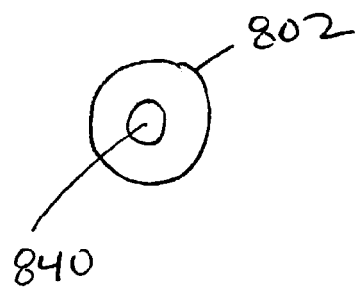
FIG. 14D illustrates a cross-sectional view taken along line D-D of the balloon catheter shown in FIG. 13B.

FIGS. 14A-14D illustrate various cross-sectional views of distal portion 810 as discussed above with respect to FIG. 13B. FIG. 14A illustrates a cross-sectional view taken along line A-A showing balloon 816, inflation lumen 830, inflation lumen 832, inflation lumen 834, and guidewire lumen 840. FIG. 14D illustrates a cross-sectional view taken along line B-B showing balloon 817, inflation lumen 832, inflation lumen 834, and guidewire lumen 840. FIG. 14C illustrates a cross-sectional view taken along line C-C showing balloon 818, inflation lumen 834, and guidewire lumen 840. FIG. 14D illustrates a cross-sectional view taken along line D-D showing catheter shaft portion 802 and guidewire lumen 840. In an alternative embodiment, balloons 816, 817, and 818 may have a common inflation lumen and still be inflated in a particular order (e.g., by controlling the rate at which the inflation medium is passed into the balloons).

Figure 15:
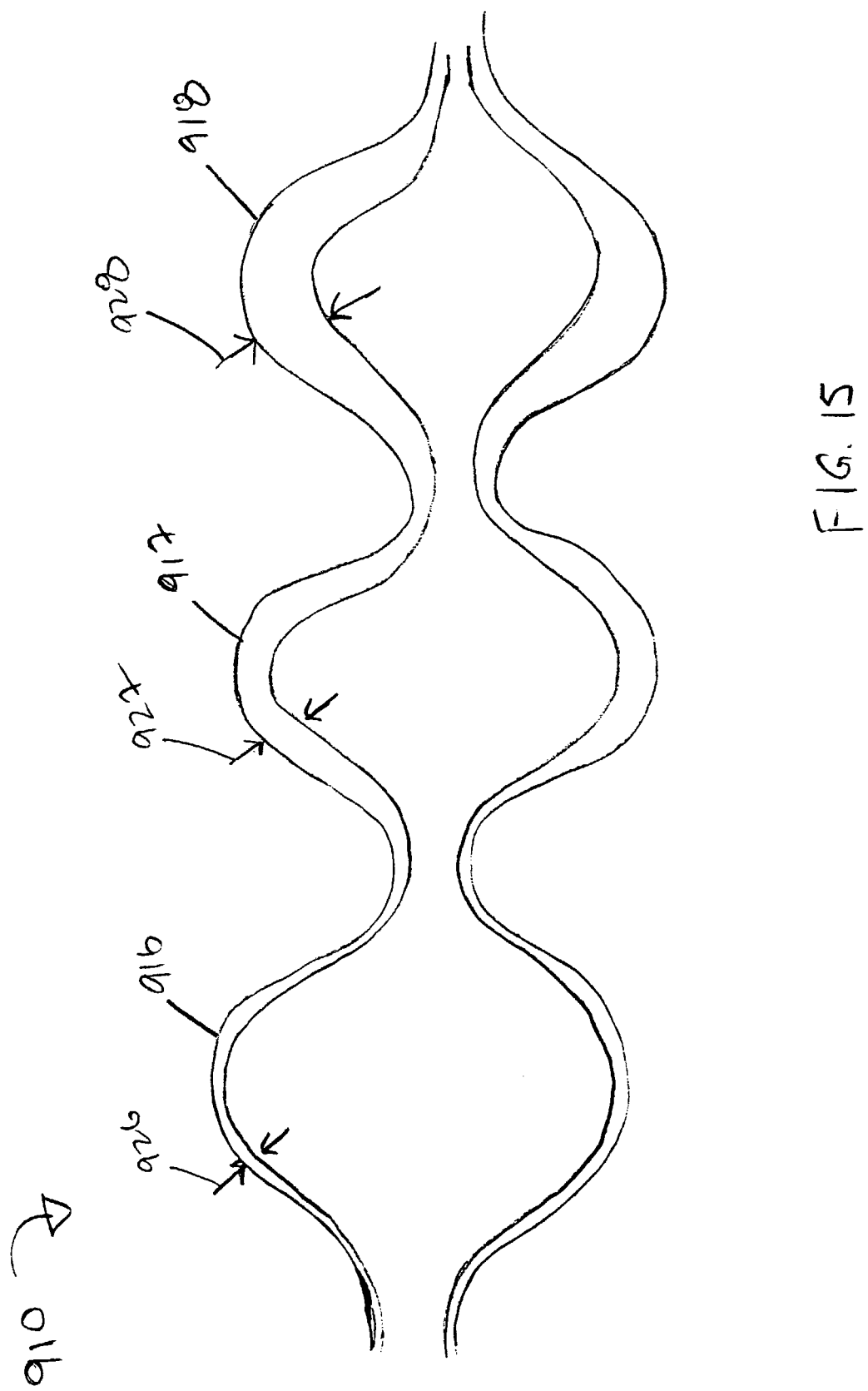
FIG. 15 illustrates another embodiment of a medical device that may be used to control the bursting of a vulnerable plaque.

FIG. 15 illustrates a view of an alternative embodiment of a multi-balloon catheter for controlling the rupture of a vulnerable plaque. A distal portion 910 may have three balloons 916, 917, and 918, with balloon 916 as the most proximal balloon and balloon 918 being the most distal balloon. Each balloon may have a predetermined thickness, for example, with balloon 916 having a thickness 926, balloon 917 having a thickness 927, and balloon 918 having a thickness 928. The thickness of each balloon increases distally from balloon 916 towards balloon 918. It should be noted that the relative thickness as shown in FIG. 15 may be exaggerated for the purpose of describing the structural properties of distal portion 910. As inflation medium is passed into the three balloons, balloon 916 inflates first followed by balloon 917 with balloon 918 inflating last. In one embodiment, balloons 916, 917, and 918 may be made of elastomeric or compliant materials, including but not limited to, Pebax®, Mylar®, Hytrel®, and Kraton®. In an alternative embodiment, other polymers may be used.

In the foregoing specification, a medical device has been described with reference to specific exemplary embodiments thereof. For example, the medical device may be used to treat other diseased sites including occluded vascular grafts or heart valves. It will, however, be evident that various modifications and changes may be made thereto without departing from the broader spirit and scope of the medical device as set forth in the appended claims. The specification and figures are, accordingly, to be regarded in an illustrative rather than a restrictive sense.

What is claimed is:

1. A method for treating a vulnerable plaque, the method comprising:
    positioning at least one balloon portion of a catheter within a blood vessel along a length of a vulnerable plaque having a cap and in a direction with a blood flow from a proximal end and a distal end of the balloon, positioning to rupture the vulnerable plaque cap near the distal end of the balloon; and
    controlling an inflation behavior of said at least one balloon to first rupture said vulnerable plaque cap near the distal end and in a same direction as said blood flow.

2. The method of claim 1, wherein positioning further comprises percutaneously advancing said catheter to said vulnerable plaque.

3. The method of claim 1, wherein controlling further comprises inflating said at least one balloon from a proximal end to a distal end.

4. The method of claim 1, wherein controlling further comprises inflating first a proximal balloon followed by a distal balloon.

5. The method of claim 1, wherein controlling comprises inflating the balloon from a proximal end of the balloon to a distal end of the balloon to squeeze the plaque from the proximal end to the distal end of the balloon.

6. The method of claim 5, wherein controlling further comprises slightly inflating the balloon to form a tapered shape from the proximal end to the distal end, substantially inflating the balloon to cause the plaque to be pushed towards the distal end of the balloon, completely inflating the balloon from its proximal end to its distal end to squeeze the plaque towards the distal end and to cause the plaque to rupture first near the distal end of the balloon.

7. The method of claim 1, wherein the balloon comprises a variable wall thickness that tapers from a proximal end of the balloon to a distal end of the balloon.

8. The method of claim 7, wherein controlling comprises first rupturing the vulnerable plaque near the distal end to squeeze the plaque lipid core out at primarily the distal edge of a lesion containing the plaque so that tissue tears are limited to primarily the distal edge but the rest of a plaque cap of the lesion is largely intact.

9. The method of claim 1, wherein controlling comprises inflating the balloon to a diameter that tapers from a proximal end of the balloon to a distal end of the balloon.

10. A method for treating a vulnerable plaque, the method comprising:
    positioning a balloon portion of a catheter within a blood vessel and adjacent to said vulnerable plaque to first rupture the vulnerable plaque near a distal end of the balloon, said balloon portion having a proximal end and the distal end; and
    inflating said balloon portion from said proximal end to said distal end to first rupture said vulnerable plaque near said distal end.

11. The method of claim 10, wherein positioning further comprises percutaneously advancing said balloon portion.

12. The method of claim 10, wherein inflating further comprises rupturing said vulnerable plaque with a direction of a blood flow within said blood vessel.

13. The method of claim 10, wherein inflating comprises inflating the balloon portion to form a tapered shape from the proximal end to the distal end.

14. The method of claim 10, wherein the balloon comprises a variable wall thickness that tapers from a proximal end of the balloon to a distal end of the balloon.

15. The method of claim 10, wherein inflating comprises inflating the balloon portion to have a diameter that tapers from the proximal end to the distal end.

16. A method for treating a vulnerable plaque, the method comprising:
    positioning at least one balloon portion of a catheter within a blood vessel along a length of a vulnerable plaque and in a direction with a blood flow to first rupture the vulnerable plaque near a distal end of the balloon, the blood flow flowing from a proximal end to the distal end of the balloon;

slightly inflating the at least one balloon to form a tapered shape of the balloon from the proximal end to the distal end of the balloon;

substantially inflating the balloon to cause the plaque to be pushed towards the distal end of the balloon; and completely inflating the balloon from its proximal end to its distal end to squeeze the plaque towards the distal end and to squeeze out near the distal end of the balloon a vulnerable plaque lipid core of the vulnerable plaque.

17. The method of claim 16 wherein substantially inflating comprises causing tissue tears of a plaque cap of vulnerable plaque to be limited primarily to a distal edge of a lesion containing the vulnerable plaque, but leaving the rest of the plaque cap largely intact.

* * * * *